US006087376A

United States Patent [19]
Crooks et al.

[11] Patent Number: 6,087,376
[45] Date of Patent: *Jul. 11, 2000

[54] USE OF LOBELINE COMPOUNDS IN THE TREATMENT OF CENTRAL NERVOUS SYSTEM DISEASES AND PATHOLOGIES

[75] Inventors: Peter A. Crooks; Linda P. Dwoskin, both of Lexington, Ky.

[73] Assignee: University of Kentucky Research Foundation, Lexington, Ky.

[*] Notice: This patent is subject to a terminal disclaimer.

[21] Appl. No.: 09/089,420

[22] Filed: Jun. 3, 1998

Related U.S. Application Data

[63] Continuation-in-part of application No. 08/795,852, Feb. 5, 1997, Pat. No. 5,830,904.
[51] Int. Cl.$^7$ .................................................. A61K 31/445
[52] U.S. Cl. ........................................... 514/317; 514/331
[58] Field of Search ...................................... 514/317, 331

[56] References Cited

U.S. PATENT DOCUMENTS

| | | | |
|---|---|---|---|
| 3,901,248 | 8/1975 | Lichtneckert et al. | 131/2 |
| 4,971,079 | 11/1990 | Talapin et al. | 131/359 |
| 5,272,144 | 12/1993 | Melloni et al. | 514/227.5 |
| 5,403,595 | 4/1995 | Kitchell et al. | 424/501 |
| 5,414,005 | 5/1995 | Schneider et al. | 514/343 |
| 5,468,755 | 11/1995 | Cincotta et al. | 514/288 |
| 5,486,362 | 1/1996 | Kitchell et al. | 424/426 |
| 5,536,503 | 7/1996 | Kitchell et al. | 424/449 |
| 5,552,429 | 9/1996 | Wong et al. | 514/415 |
| 5,576,321 | 11/1996 | Krushinski, Jr. et al. | 514/255 |

FOREIGN PATENT DOCUMENTS

WO92/19241  11/1992  WIPO.

OTHER PUBLICATIONS

Levin, E.D., Drug Dev. Res., 38(3–4), 188–95 (abstract), 1996.

Barlow, R.B. et al., "Relationship between structure and nicotine–like activity: X–ray crystal structure analysis of (–)cytisine and (–)lobeline hydrochloride and a comparison with (–)nicotine and other nicotine–like compounds," *Br. J. Pharmacol.*, 98:799–808 (1989).

Brownstein, M.J. et al., "Neurotransmitter transporters," *Rec. Prog. Hormone Res.*, 49:27–42 (1994).

Debler, E.A. et al., "Ascorbic acid and striatal transport of [$^3$H]1–methyl–4–phenylpyridine (MPP$^+$) and [$^3$H]dopamine," *Life Sci.*, 42:2553–2559 (1988).

Floor, E. et al., "Dynamic storage of dopamine in rat brain synaptic vesicles in vitro," *J. Neurochem.* 64, 689–699 (1995).

Liu Y. et al., "A molecular analysis of vesicular amine transporter," *Behav. Brain Res.* 73, 51–58 (1996).

Scherman, D., "Dihydrotetrabenazine binding and monoamine uptake in mouse brain regions," *J. Neurochem.* 47, 331–339 (1986).

Scherman, D. et al., "The regionalization of [$^3$H]dihydrotetrabenazine binding sites in the mouse brain and its relationship to the distribution of monoamines and their metabolites," *Brain Res.* 370, 176–181 (1986).

Scherman, D. et al., "[$^3$H]Dihydrotetrabenazine, a new in vitro monoaminergic probe for human brain," *J. Neurochem.* 50, 1131–1136 (1988).

Standaert, D.G. et al., "Treatment of central nervous system degenerative disorders," *The Pharmacological Basis of Therapeutics*, 9th ed. (Hardman J.G., Limberd L.E., Molinoff P.B., Ruddon R.W., and Gilman A.G., eds.), pp. 503–519, McGraw–Hill, New York (1996).

Olin, B.R. et al., "Smoking Deterrents," In *Drug Facts and Comparisons*. 1995 edition, ed. by B.R. Olin et al., pp. 3087–3095, St. Loius, MO: J.B. Lippincott Co., 1995.

Sloan, J.W. et al., "The comparative binding characteristics of nicotinic ligands and their pharmacology," *Pharmacol. Biochem. Behav.*, 30:255–267 (1988).

Hamann, S.R. et al., "Hyperalgesic and analgesic actions of morphine, U50–488, naltrexone, and (–)lobeline in the rat brainstem," *Pharmacol. Biochem. Behav.*, 47:197–201 (1994).

Brioni, J.D. et al., "Nicotinic receptor agonists exhibit anxiolytic–like effects on the elevated plus–maze test," *Eur. J. Pharmacol.*, 238:1–8 (1993).

Decker, M.W. et al., "Effects of lobeline, a nicotinic receptor agonist, on learning and memory," *Pharmacol. Biochem. Behav.*, 45:571–576 (1993).

(List continued on next page.)

*Primary Examiner*—Phyllis G. Spivack
*Attorney, Agent, or Firm*—McDermott, Will & Emery

[57] ABSTRACT

Lobeline and nicotine evoke [$^3$H]overflow from rat striatal slices preloaded with [$^3$H]dopamine ([$^3$H]DA). The lobeline-evoked overflow is calcium-independent and not antagonized by mecamylamine, suggesting a mechanism of action other than the stimulation of nicotinic receptors. Whereas nicotine stimulates nicotinic receptors, lobeline inhibits [$^3$H]DA uptake into synaptic vesicles and striatal synaptosomes. The results suggest that different mechanisms are responsible for the increase in striatal DA release evoked by lobeline and nicotine. [$^3$H]-Dihydrotetrabenazine [$^3$H]DTBZ), used routinely to probe a high-affinity binding site-on the vesicular monoamine transporter (VMAT2) binds to vesicle membranes from rat striatum. Lobeline inhibits [$^3$H]DTBZ binding with an IC$_{50}$ of 0.90 μM, consistent with its IC$_{50}$ of 0.88 μM for inhibition of [$^3$H]DA uptake into vesicles. These results suggest that the action of lobeline is similar to that of amphetamine and that it specifically interacts with DTBZ sites on VMAT2 to inhibit DA uptake into synaptic vesicles. d-amphetamine inhibits [$^3$H]DTBZ binding to vesicle membranes with an IC$_{50}$ of 39.4 μM, a concentration 20 times greater than reported for inhibition of VMAT2 function, suggesting that d-amphetamine interacts with a different site than lobeline on VMAT2 to inhibit monoamine uptake. These results suggest the use of lobeline and analogs thereof in treating individuals for diseases and pathologies of the central nervous system.

13 Claims, 12 Drawing Sheets

OTHER PUBLICATIONS

Nunn–Thompson et al., "Pharmacotherapy for smoking cessation," *Clin. Pharmacy.*, 8:710–720 (1989).

Prignot, J., "Pharmacological approach to smoking cessation," *Eur. Respir. J.*, 2:550–560 (1989).

Kalyuzhnyy, V.V., "The treatment of nicotinism with the aid of lobeline and its influence on vegetative and vascular reactions," *J. Neural. Psychiat.*, 68:1864–1870 (1968).

Stolerman, I.P. et al., "Dissociation between the locomotor stimulant and depressant effects of nicotinic agonists in rats," *Psychopharmacol.*, 117:430–437 (1995).

Fudala, P.J. et al., "Further studies on nicotine–induced conditioned place preference in the rat," *Pharmacol. Biochem. Behav.*, 25:1041–1049 (1986).

Geller, I. et al., "Effects of nicotine monomethiodide, lobeline, chlordiazepoxide, meprobamate and caffeine on a discrimination task in laboratory rats," *Psychopharmacol. (Berl.)*, 20:355–365 (1971).

Schechter, M.D. et al., "Nicotine as a discriminative cue in rats: inability of related drugs to produce a nicotine–like cuing effect," *Psychopharmacol. (Berl.)*, 27:379–387 (1972).

Reavill, C. et al., "Behavioral and pharmacokinetics studies on nicotine, cytosine and lobeline," *Neuropharmacol.*, 29(7):619–624 (1990).

Romano, C. et al., "Sterespecific nicotine receptors on rat brain membranes," *Science*, 210:647–650 (1980).

Decker, M.W. et al., "Diversity of neuronal nicotinic acetylcholine receptors: lessons from behavior and implications for CNS therapeutics" *Life Sci.*, 56:545–570 (1995).

Yamada, S. et al., "Brain nicotinic acetylcholine receptors biochemical characterization by neosurugatoxin," *Mol. Pharmacol.*, 28:120–127 (1985).

Lippiello, P.M. et al., "The binding of L–[$^3$H]nicotine to a single class of high affinity sites in rat brain membrane," *Mol. Pharmacol.*, 29:448–454 (1986).

S. Martin et al., "Opioid and nicotinic medellary hyperalgesic influences in the decerebrated rat," *Pharmacol Biochem and Behav.*, 29 725–721 1988.

Broussolle, E.P. et al., "In vivo binding of $^3$H–nicotine in the mouse brain," *Life Sci.*, 44:1123–1132 (1989).

Bhat, R.V. et al., "Regulation of brain nicotinic receptors by chronic agonist infusion," *J. Neurochem.*, 56(6):1932–1939 (1991).

Sakurai, Y. et al., "Enhancement of [$^3$H]dopamine release and its [$^3$H]metabolites in rat striatum by nicotinic drugs," *Brain Res.*, 242:99–106 (1982).

Takano, Y. et al., "Presynaptic modulation of the release of dopamine from striatal synaptosomes: difference in the effects of High K$^+$ stimulation, methamphetamine and nicotinic drugs," *Brain Res.*, 279:330–334 (1983).

Grady, S. et al., "Characterization of nicotine receptor–mediated $^3$H–dopamine release from synaptosomes prepared from mouse striatum," *J. Neurochem.*, 59:848–856 (1992).

USE OF LOBELINE COMPOUNDS IN THE TREATMENT OF CENTRAL NERVOUS SYSTEM DISEASES AND PATHOLOGIES

REFERENCE TO RELATED APPLICATION

This application is a continuation-in-part of U.S. patent application Ser. No. 08/795,852, filed Feb. 5, 1997 U.S. Pat. No. 5,830,904.

FIELD OF THE INVENTION

The present invention relates to the use of lobeline and analogs thereof in the treatment of diseases and pathologies of the central nervous system (CNS). The invention also relates to the treatment of drug abuse and withdrawal therefrom, as well as eating disorders, such as obesity.

BACKGROUND OF THE INVENTION

Lobeline (α-lobeline) is a lipophilic, non-pyridino, alkaloidal constituent of Indian tobacco (Lobelia inflata). As shown by the following formulas, no obvious structural resemblance to S(−)nicotine is apparent:

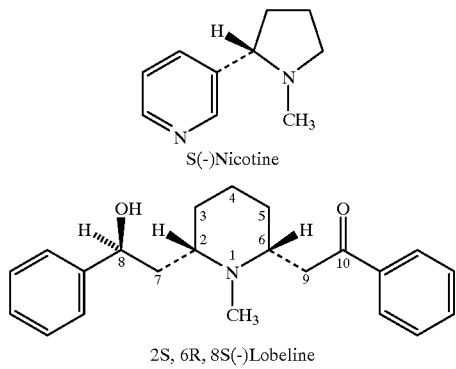

S(-)Nicotine 2S, 6R, 8S(-)Lobeline

Structure-function relationships between nicotine and lobeline do not suggest a common pharmacophore (Barlow and Johnson, 1989). Nonetheless, lobeline has been reported to have many nicotine-like effects including tachycardia and hypertension (Olin et al., 1995), bradycardia and hypotension in urethane and pentobarbital anesthetized rats (Sloan et al., 1988), hyperalgesia (Hamann and Martin, 1994), anxiolytic activity (Brioni et al., 1993), and improvement of learning and memory (Decker et al., 1993). Moreover, lobeline has been used as a substitution therapy for tobacco smoking cessation (Nunn-Thompson and Simon, 1989; Prignot, 1989; Olin et al., 1995); however, its effectiveness is controversial as reflected by both positive (Dorsey, 1936; Kalyuzhnyy, 1968) and negative reports (Wright and Littauer, 1937; Nunn-Thompson and Simon, 1989). Furthermore, only short-term usage of lobeline as a smoking deterrent has been recommended due to its acute toxicity (nausea, severe heartburn and dizziness) and the lack of information concerning its long-term usage (Wright and Littauer, 1937; Olin et al., 1995).

In behavioral studies, nicotine has been shown to increase locomotor activity (Clarke and Kumar, 1983a, 1983b; Clarke, 1990; Fung and Lau, 1988), and to produce conditioned place preference (Shoaib et al., 1984); Fudala et al., 1985) in rats. However, the results of the latter studies are controversial (Clarke and Fibiger, 1987). In contrast, lobeline does not increase locomotor activity (Stolerman et al., 1995) or produce conditioned place preference (Fudala and Iwamoto, 1986). Although initially lobeline was shown to generalize to nicotine in discrimination studies (Geller et al., 1971), most subsequent studies have failed to reproduce this original finding (Schechter and Rosecrans, 1972; Reavill et al., 1990; Romano and Goldstein, 1980).

Nicotine has been reported to be avidly self-administered by rats (Corrigal et al. 1992, 1994; Donny et al., 1996); however, the ability of lobeline to support self-administration has not been investigated. Based on the differential effects of lobeline and nicotine in behavioral studies, it appears that these drugs may not be acting via a common CNS mechanism, even though lobeline is often considered to be a nicotinic agonist (Decker et al., 1995).

The positive reinforcing effect of nicotine is believed to be due to the activation of central dopaminergic systems (Bowell and Balfour, 1992; Corrigal et al., 1992, 1994). Presynaptic nicotinic receptors have been found on dopamine (DA)-containing nerve terminals (Giorguieff-Chesselet et al., 1979; Clarke and Pert, 1985). Nicotine binds to nicotinic receptors with high affinity ($Kd=1-7$ nM) (Lippiello and Fernandes, 1986; Reavill et al., 1988; Romm et al., 1990; Bhat et al., 1991; Loiacono et al., 1993; Anderson and Arneric, 1994). Also, lobeline has been reported to displace [$^3$H]nicotine binding from central nicotinic receptors with high affinity ($Ki=5-30$ nM) (Yamada et al., 1985; Lippiello and Fernades, 1986; Banerjee and Abood, 1989; Broussolle et al., 1989).

Chronic treatment with nicotine results in an increase in the number of nicotinic receptors in many regions of rat and mouse brain (Collins et al., 1990; Bhat et al., 1991, 1994; Marks et al., 1992; Sanderson et al., 1993). An increase in the number of nicotinic receptors in postmortem human brain tissue obtained from smokers also has been reported (Benwell et al., 1988). In contrast, chronic lobeline administration did not increase the number of nicotinic receptors in mouse brain regions in which increases were observed following chronic nicotine administration (Bhat et al., 1991).

Nicotine evokes DA release in in vitro superfusion studies using striatal slices (Westfall, 1974; Giorguieff-Chesselet et al., 1979; Westfall et al., 1987; Harsing et al., 1992) and striatal synaptosomes (Chesselet, 1984; Rowell et al., 1987; Rapier et al., 1988, 1990; Grady et al., 1992, 1994; Rowell and Hillebrand, 1992, 1994; Rowell, 1995), and in in vivo studies using microdialysis in striatum (Imperato et al., 1986; Damsma et al., 1989; Brazell et al., 1990; Toth et al, 1992). Nicotine-evoked DA release is calcium-dependent, mecamylamine-sensitive and mediated by nicotinic receptors (Giorguieff-Chesselet et al., 1979; Westfall et al, 1987; Rapier et al., 1988; Grady et al., 1992). Mecamylamine is a noncompetitive nicotinic receptor antagonist, which more effectively blocks the ion channel of the receptor (Varanda et al., 1985; Loiacono et al., 1993; Peng et al., 1994). Similar to nicotine, lobeline has been reported to increase DA release from superfused rat and mouse striatal synaptosomes (Sakurai et al., 1982; Takano et al, 1983; Grady et al., 1992). Based on these neurochemical studies, lobeline was suggested to be an agonist at nicotinic receptors (Decker et al., 1995). It is difficult to reconcile that nicotine and lobeline similarly release DA and displace [$^3$H]nicotine binding; however, the observed upregulation of nicotinic receptors following chronic nicotine administration is not observed following chronic lobeline administration.

Earlier studies of the pharmacokinetic properties of lobeline have centered on its proposed use in the treatment of nicotinism. For example, U.S. Pat. Nos. 5,536,503; 5,486, 362; 5,403,595; and PCT Publication WO 92/19241 are all related to a drug delivery system and method for treating nicotine dependence. U.S. Pat. Nos. 5,414,005; 4,971,079; and 3,901,248 also discuss the use of lobeline in the context of treating nicotine abuse and/or addiction. A scientific article has studied the actions of morphine, lobeline, and other drugs in inducing "analgesia" in rats (S. Hamann et al. 1994). However, these workers did not equate their finding of an "analgesic" response for lobeline to a reduction of the pain response in man, nor did they propose the use of lobeline in treating drug abuse, withdrawal from addiction, and the like.

Similarly, to the present inventors' knowledge, the use of lobeline in the treatment of eating disorders has not been proposed. This is in spite of the widely accepted ability of nicotine to suppress appetite (see, e.g., Remington's Pharm. Sci., 18th ed., p.891) and the previously proposed association of obesity with reduced bioavailability of dopamine (U.S. Pat. Nos. 5,552,429; 5,576,321; 5,272,144; and 5,468,755).

The present study further elucidates the mechanism of action of lobeline using [$^3$H]dihydrotetrabenazine ([$^3$H] DTBZ), a structural analog of tetrabenazine (TBZ), which binds to a single class of high-affinity sites on the vesicular monoamine transporter-2 protein (VMAT2) to inhibit vesicular DA uptake (Pletscher et al., 1962; Scherman et al., 1986; Kilbourn et al., 1995; Liu et al., 1996). Of note, TBZ does not alter spontaneous efflux of [$^3$H]DA from rat brain vesicles (Floor et al., 1995). Taken together, TBZ appears to block [$^3$H]DA uptake into vesicles but does not promote [$^3$H]DA release from vesicles.

In the present study, the effect of lobeline is compared with that of d-amphetamine, a psychostimulant and lipophilic weak base reported to inhibit DA uptake into striatal synaptic vesicles (Philippu and Beyer, 1973; Ary and Komiskey, 1980) and to inhibit monoamine uptake into human VMAT2 expressed in CV-1 cells (Erickson et al., 1996). d-Amphetamine has also been reported to release DA from synaptic vesicles of the Planorbis corneus giant DA cell, increasing DA concentrations in the cytosol and promoting reverse transport of DA via DAT (Sulzer and Rayport, 1990; Sulzer et al., 1995). Furthermore, d-amphetamine has been reported to inhibit [$^3$H]DTBZ binding to rat striatal homogenates (Rostene et al., 1992) and human VMAT2 expresed in COS cells (Gonzalez et al., 1994), but with low potency. The ability of lobeline to evoke [$^3$H]DA release from rat striatal synaptic vesicles preloaded with [$^3$H]DA is also assessed in the present study.

SUMMARY OF THE INVENTION

The present invention is for a method of treating an individual who suffers from a disease or pathology of the central nervous system (CNS). The method comprises administering to the individual an amount of a lobeline compound, i.e., lobeline, analogs, and derivatives thereof, including pharmaceutically acceptable salts. The amount of lobeline compound administered is effective to alleviate at least one of the symptoms of the individual's condition.

The lobeline compound can be administered alone, combined with an excipient, or coadministered with a second drug having a similar or synergistic effect. The compound or composition is preferably administered subcutaneously, intramuscularly, intravenously, transdermally, orally, intranasally, or rectally.

The utility of lobeline, analogs, and derivatives thereof, e.g., those that form lobeline upon metabolism by the body, in treating dependencies on drugs of abuse is implicated by the present studies. In particular, the treatment of dependencies on such drugs as cocaine, amphetamines, caffeine, phencyclidine, opiates, barbiturates, benzodiazepines, cannabinoids, hallucinogens, and alcohol is implicated. Also, the treatment of eating disorders, such as obesity, is implicated. In a preferred aspect of the invention, the method of treatment reduces an individual's desire for the drug of abuse or for food by at least one day.

A lobeline compound of the present invention is contemplated primarily for use in the treatment of diseases and pathologies associated with the CNS. Thus, cognitive disorders, head or brain trauma, memory loss, psychosis, sleep disorders, obsessive-compulsive disorders, panic disorders, myasthenia gravis, Parkinson's disease, Alzheimer's disease, schizophrenia, Tourette's syndrome, Huntington's disease, and attention deficit disorder, and related conditions are considered to be susceptible to treatment with a lobeline compound of the present invention.

As shown by the results of the studies described herein, and contrary to conventional belief, lobeline is found to act at higher concentrations primarily not as a nicotinic agonist, but by a different mechanism than is observed for nicotine. The present studies also suggest that lobeline may be effective in inhibiting uptake of extracellular dopamine by cells of the CNS, perhaps by blocking dopamine receptors on the cells. Either or both mechanisms can thereby work to increase the extracellular concentration of dopamine. Many respects in which the actions of lobeline are similar to those of amphetamine have been identified.

BRIEF DESCRIPTION OF THE FIGURES

FIG. 2A illustrates the time course of the fractional release evoked by low concentrations (0.01–3 μM) of lobeline, and FIG. 2B illustrates that evoked by high concentrations (3–100 μM). *P<0.05, different from basal outflow; +P<0.05, different from the peak responses at 25 min for 0.01–3 μM and 30–300 μM; §P<0.05, different from the peak responses of 0.01–10 μM and 100 μM;

P<0.05, different from the peak responses of 0.01–30 $\mu$M; Fisher's LSD post hoc test. n=6 rats.

Figure 3:
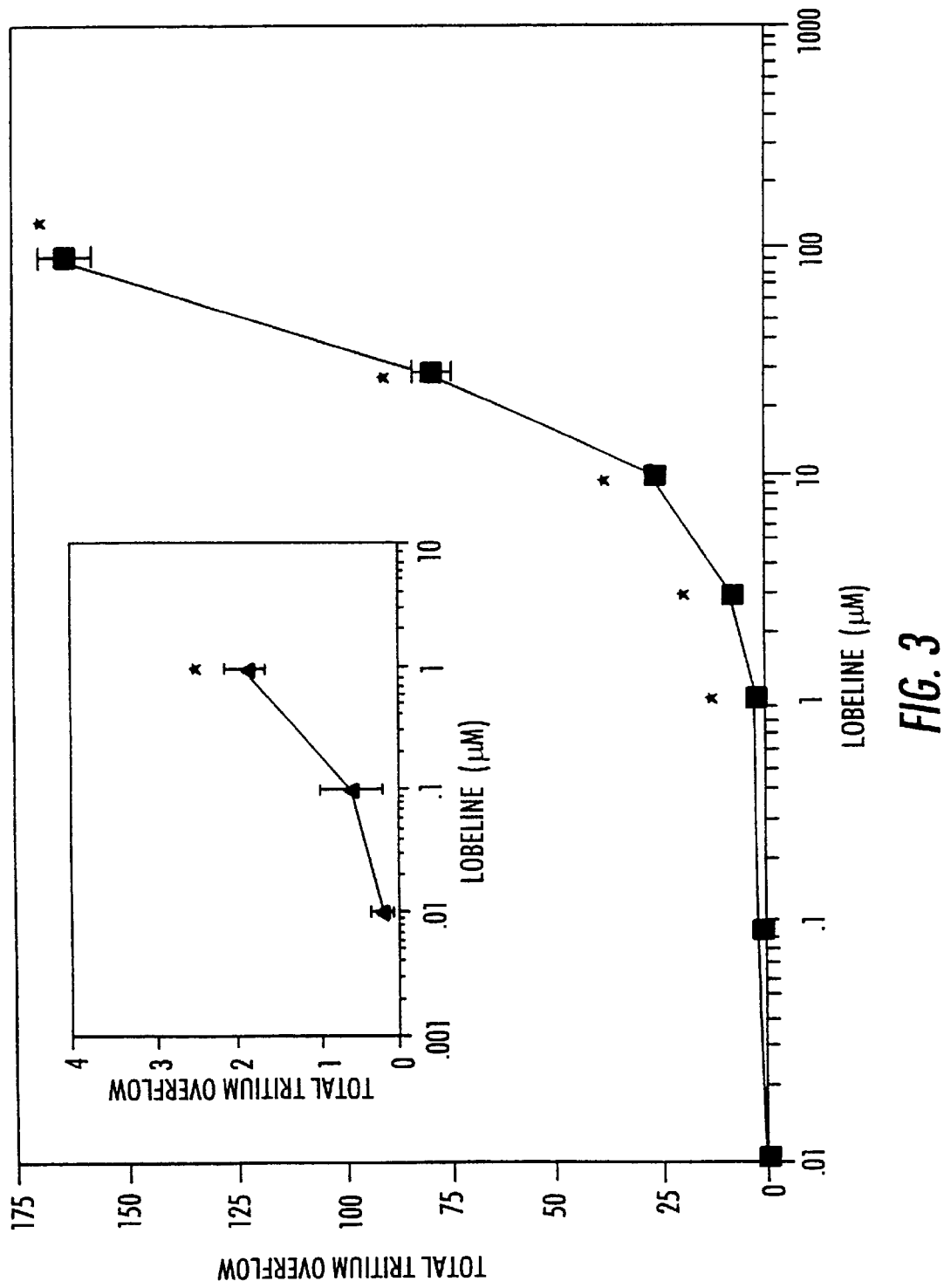

FIG. 3 depicts the concentration-dependence of lobeline-evoked total [$^3$H]overflow from rat striatal slices preloaded with [$^3$H]DA. Data are presented as mean±S.E. total [$^3$H] overflow, which represents the area under the curve of the corresponding lobeline concentration-response as a function of time. The inset illustrates the total [$^3$H]overflow evoked by the lower concentrations (0.01–1 $\mu$M) of lobeline. Control slices which were superfused with buffer in the absence of lobeline did not evoke [$^3$H]overflow (i.e. fractional release was not different from basal during the course of superfusion). *P<0.05, different from control and each of the other lobeline concentrations; Duncan's New Multiple Range Test. n=6 rats.

Figure 4:
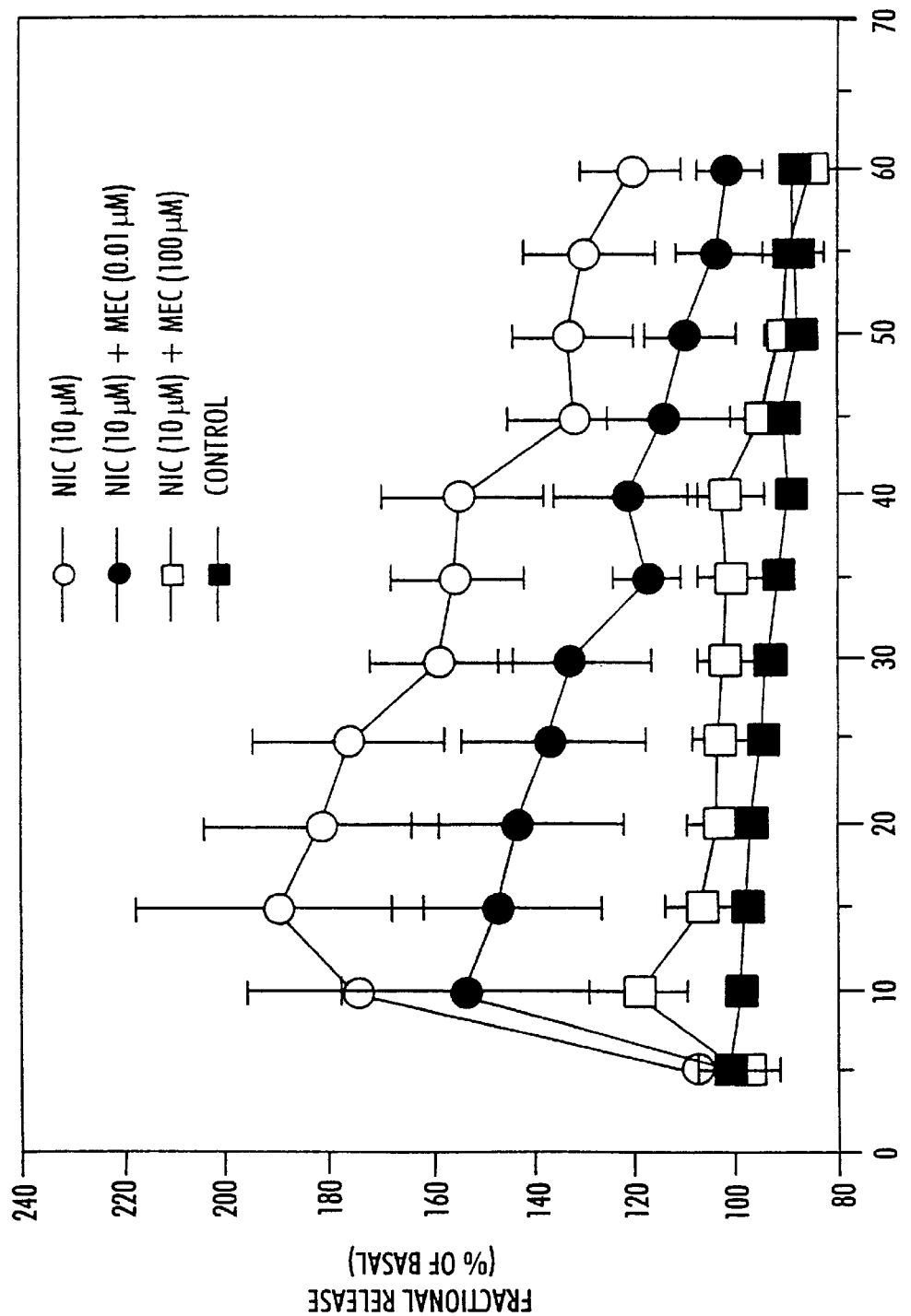

FIG. 4 depicts the time course of the effect of mecamylamine to inhibit nicotine(10 $\mu$M)-evoked fractional release of [$^3$H]DA from preloaded rat stratal slices. For clarity of graphical presentation, only significant effects of the lowest and highest concentration, 0.01 and 100 $\mu$M, respectively, of mecamylamine are illustrated. Data are presented as mean±S.E. fractional release as percentage of basal outflow. Experiments were performed as described in Table 2 hereinbelow. The time course begins at the time of nicotine (10 $\mu$M) addition to the superfusion buffer containing mecamylamine. The control represents fractional release in the absence of either mecamylamine or nicotine in the superfusion buffer. Duncan's New Multiple Range Test revealed a significant inhibitory effect of 0.01 $\mu$M mecamylamine, when the data were collapsed across time of superfusion. n=8 rats.

Figure 5:
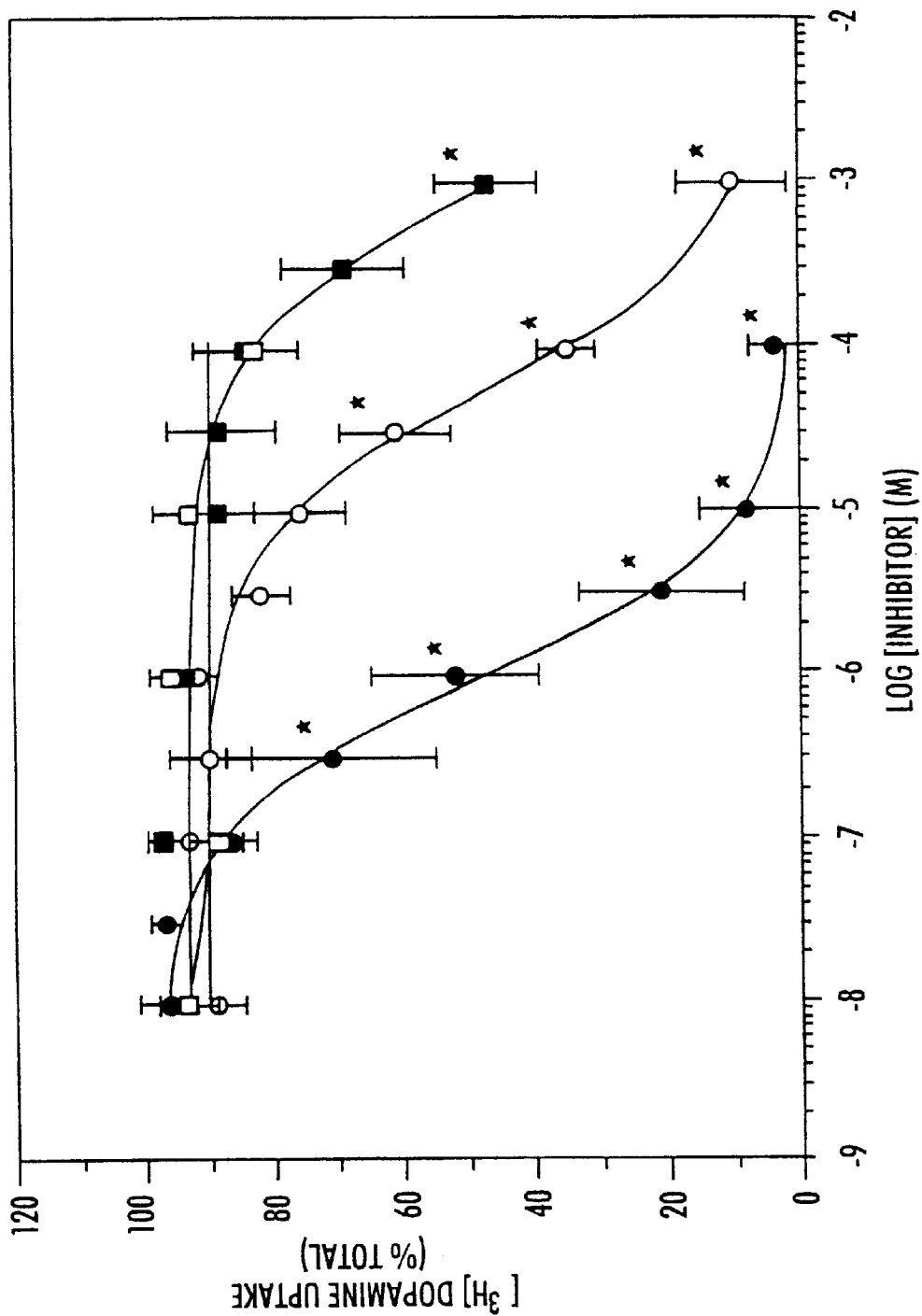

FIG. 5 depicts the effects of nicotine (0.01–1000 $\mu$M) and lobeline (0.01–1000 $\mu$M) on rat striatal synaptosomal and synaptic vesicular [$^3$H]DA uptake. □ nicotine, synaptosomal [$^3$H]DA uptake; ■ nicotine, vesicular [$^3$H]DA uptake; O lobeline, synaptosomal [$^3$H]DA uptake; ● lobeline, vesicular [$^3$H]DA uptake. Data are presented as mean±S.E. percentage of total [$^3$H]DA uptake. Total [$^3$H]DA uptake for synaptosomes and vesicles was 109±9.80 pmol/min/mg and 1340±71.7 pmol/min/mg, respectively. Non-specific [$^3$H] DA uptake in synaptosomal and vesicular experiments was 2% and 20%, respectively, of total [$^3$H]DA uptake as determined by incubation with 10 $\mu$M GBR and incubation at 0° C., respectively. Experiments examining the effect of nicotine on synaptosomal uptake included a low concentration range (0.001–1 nM), however, no effect was observed and for clarity of graphical presentation these results are not illustrated. *P<0.05, different from total [$^3$H]DA uptake; Dunnett's post hoc test. n=3–6 rats.

Figure 6:
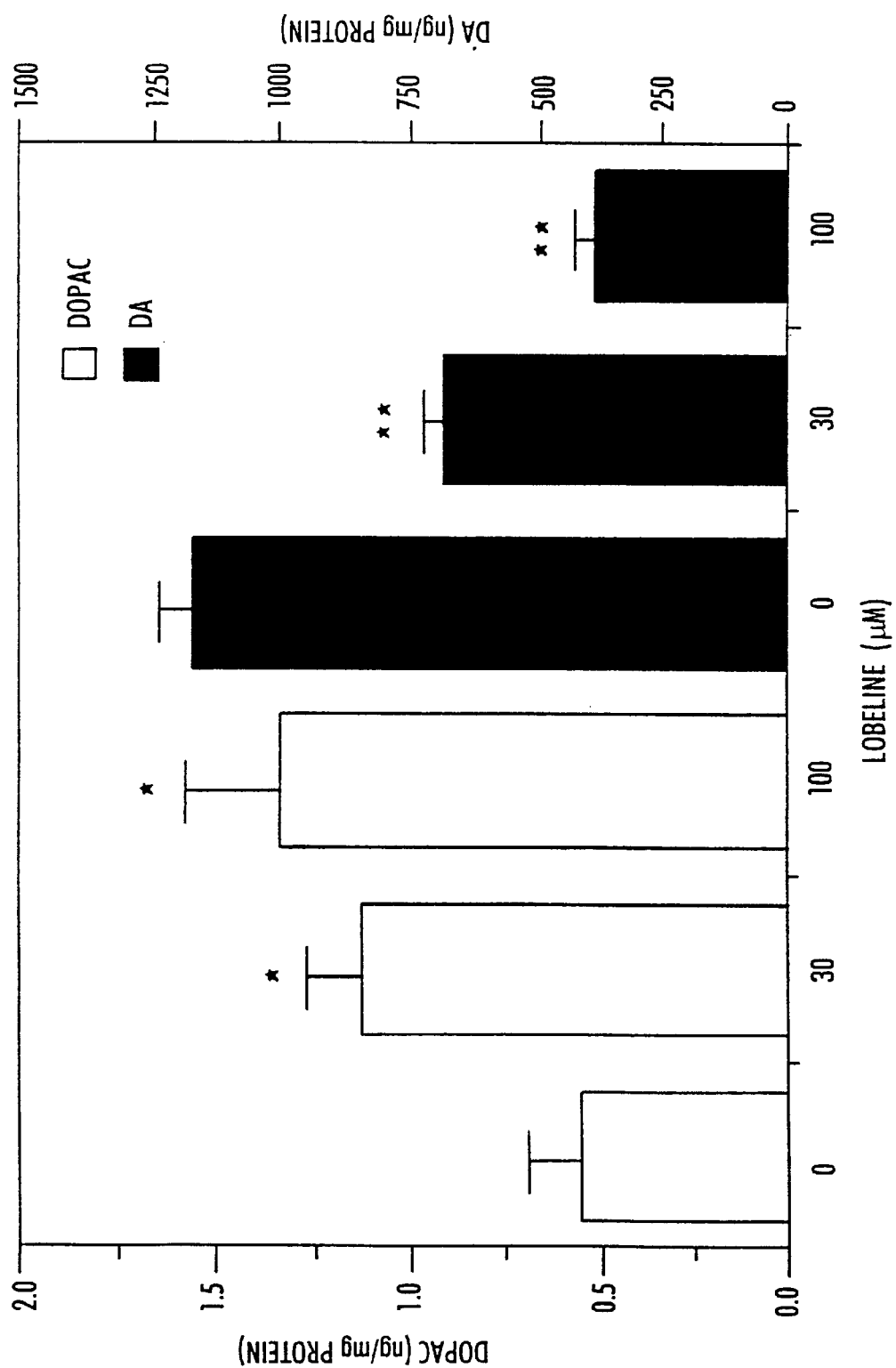

FIG. 6 depicts the endogenous DA and DOPAC (dihydroxyphenylacetic acid) content in rat striatal slices superfused with high concentrations (30–100 $\mu$M) of lobeline. Endogenous DA and DOPAC content were determined after 60 min superfusion with various concentrations of lobeline. Data are presented as mean±S.E. ng/mg protein. *P<0.05, different from control, P<0.05, **P<0.001, different from control; Dunnett's post hoc test. n=8 rats.

Figure 7:
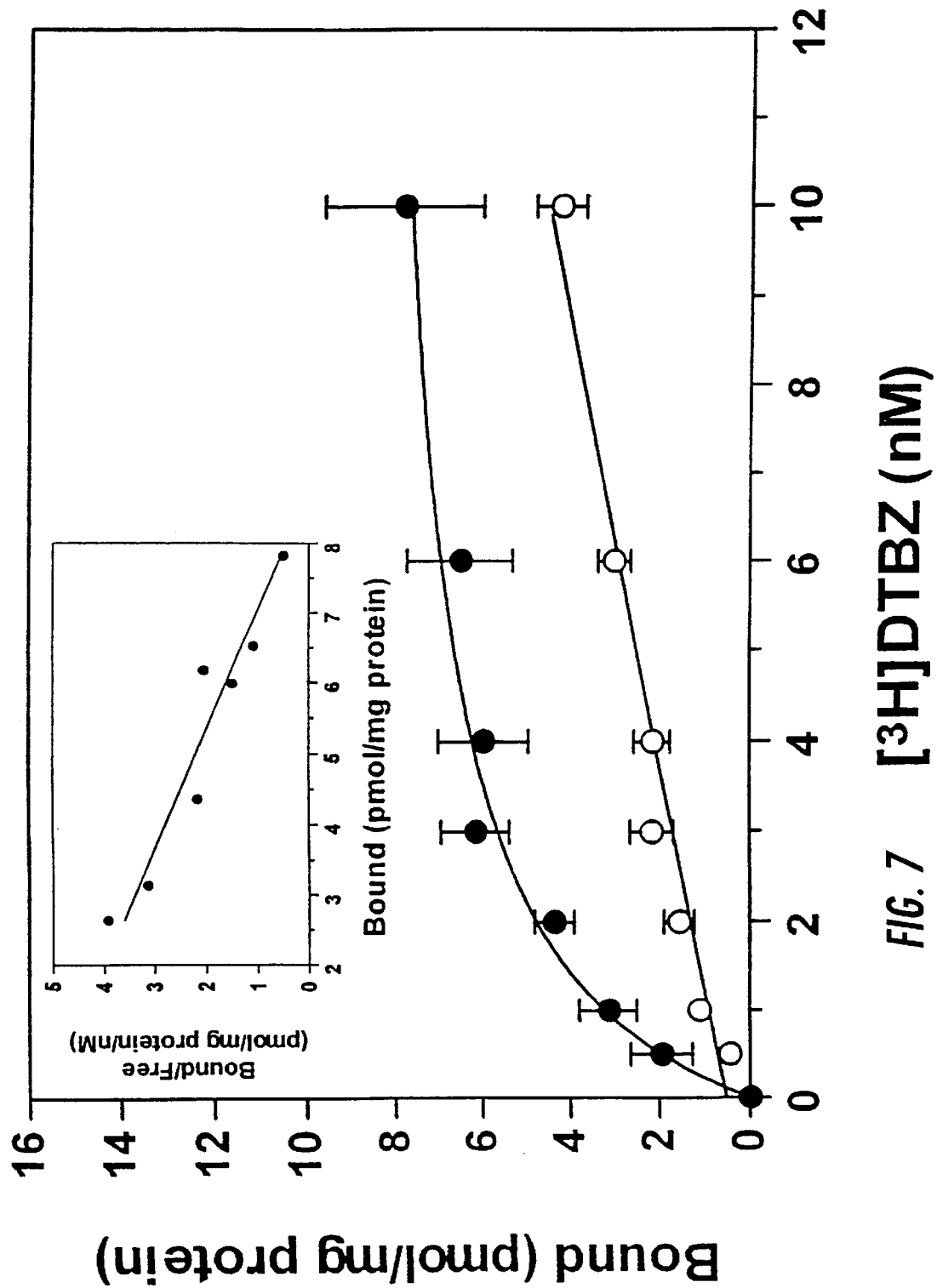

FIG. 7 depicts equilibrium binding of [$^3$H]DTBZ to rat striatal vesicles. Striatal vesicles were incubated for 10 min at 25° C. in the absence and presence of [$^3$H]DTBZ (0.5–10 nM) Nonspecific binding (○) was determined using 20 $\mu$M TBZ. Specific binding (●) was defined as the difference between total binding (not shown) and the nonspecific binding. Data are mean±SEM pmol/mg protein. Inset: Scatchard transformation of the mean specific [$^3$H]DTBZ binding data from the saturation analyses. n=4 experiments.

Figure 8:
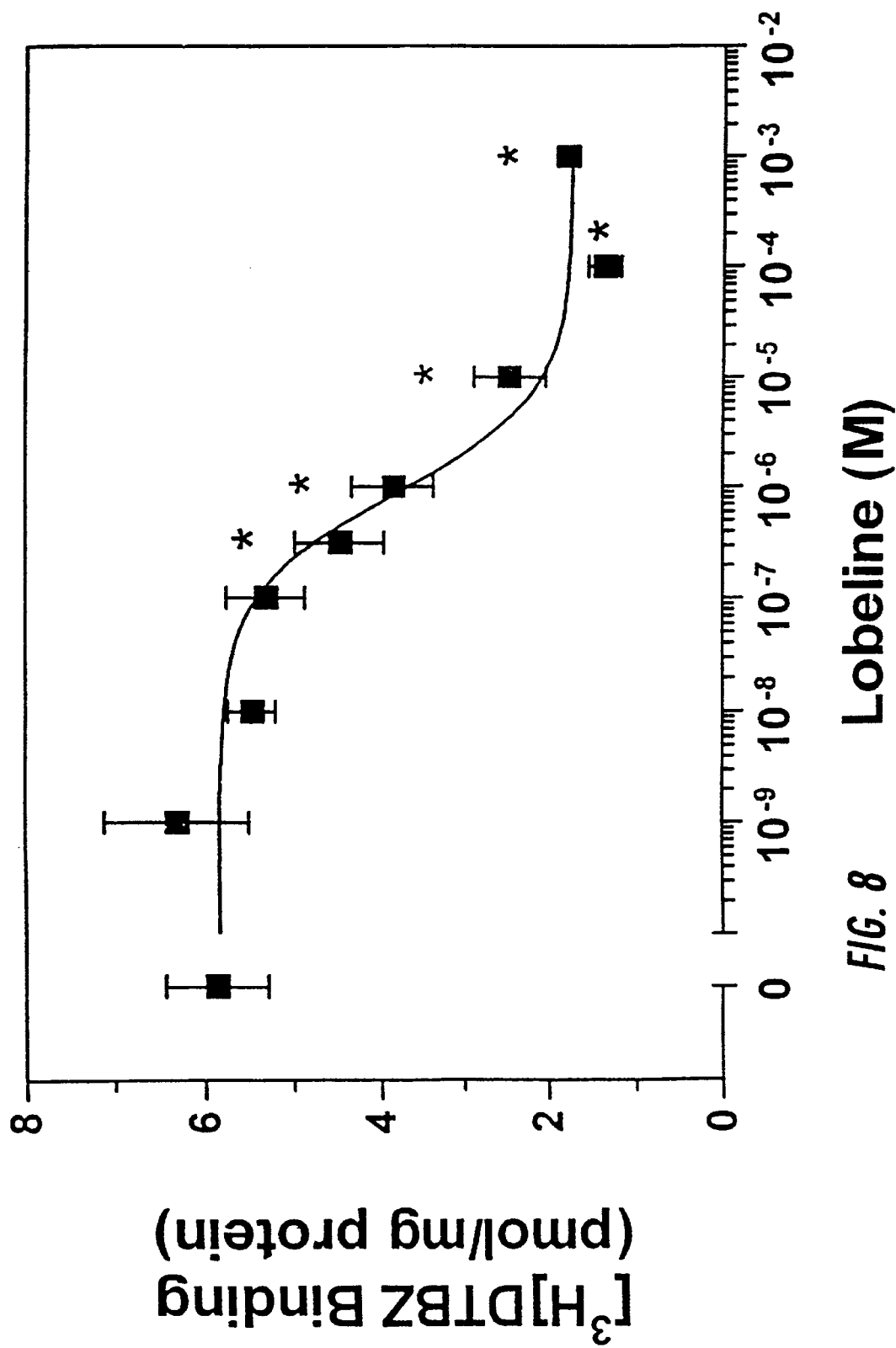

FIG. 8 depicts lobeline inhibition of [$^3$H]DTBZ binding to rat striatal vesicles. Data represent the mean±SEM pmol [$^3$H]DTBZ bound/mg protein. Control represents the amount of [$^3$H]DTBZ bound in the absence of lobeline. *p<0.05, significantly different from control; Fisher least significant difference post hoc test. n=5 experiments.

Figure 9:
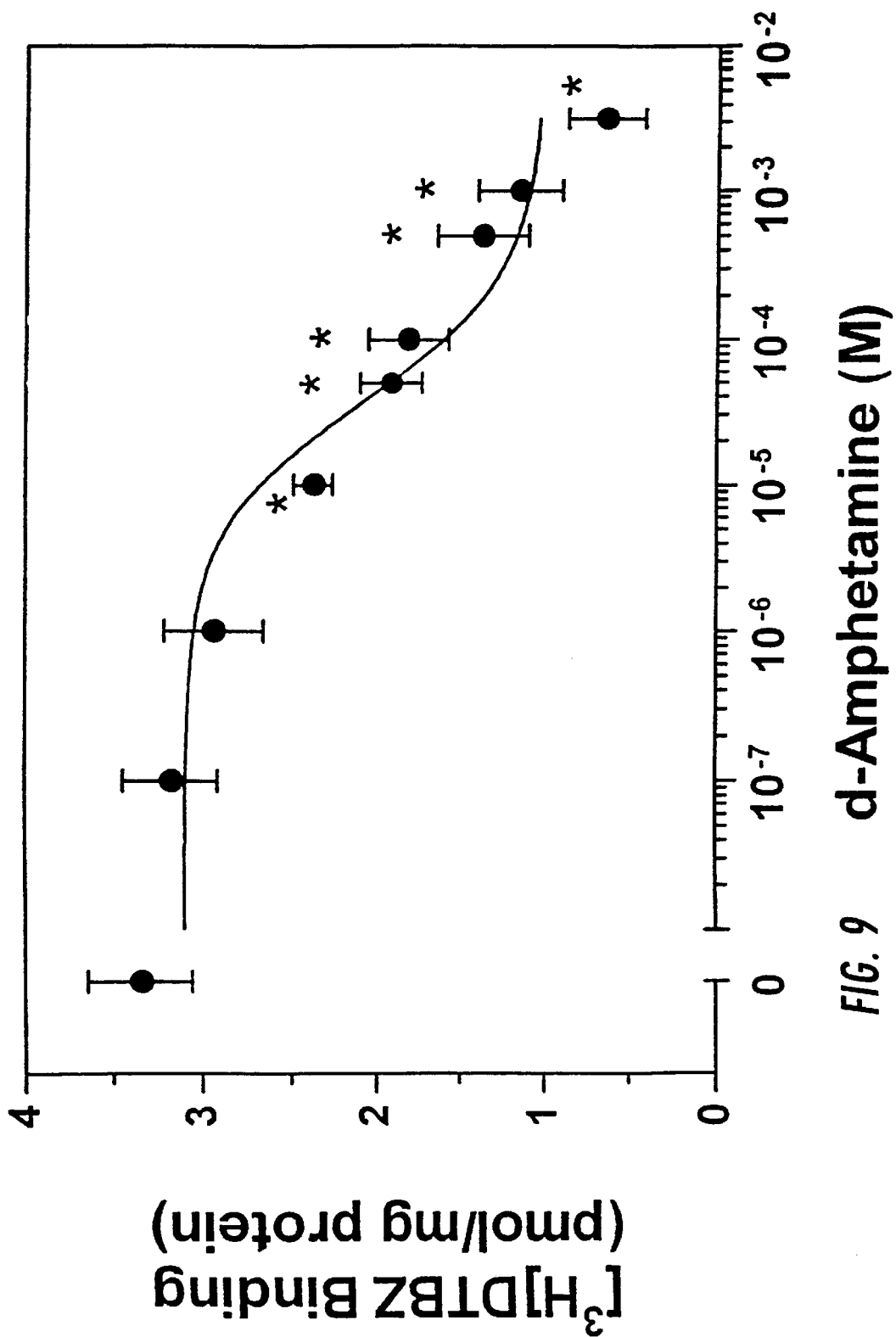

FIG. 9 shows that d-amphetamine inhibits [$^3$H]DTBZ binding to rat striatal vesicles. Data represent the mean±SEM pmol [$^3$H]DTBZ bound/mg protein. Control represents the amount of [$^3$H]DTBZ bound in the absence of d-amphetamine. *p<0.05, significantly different from control; Fisher least significant difference post hoc test. n=5 experiments.

Figure 10:
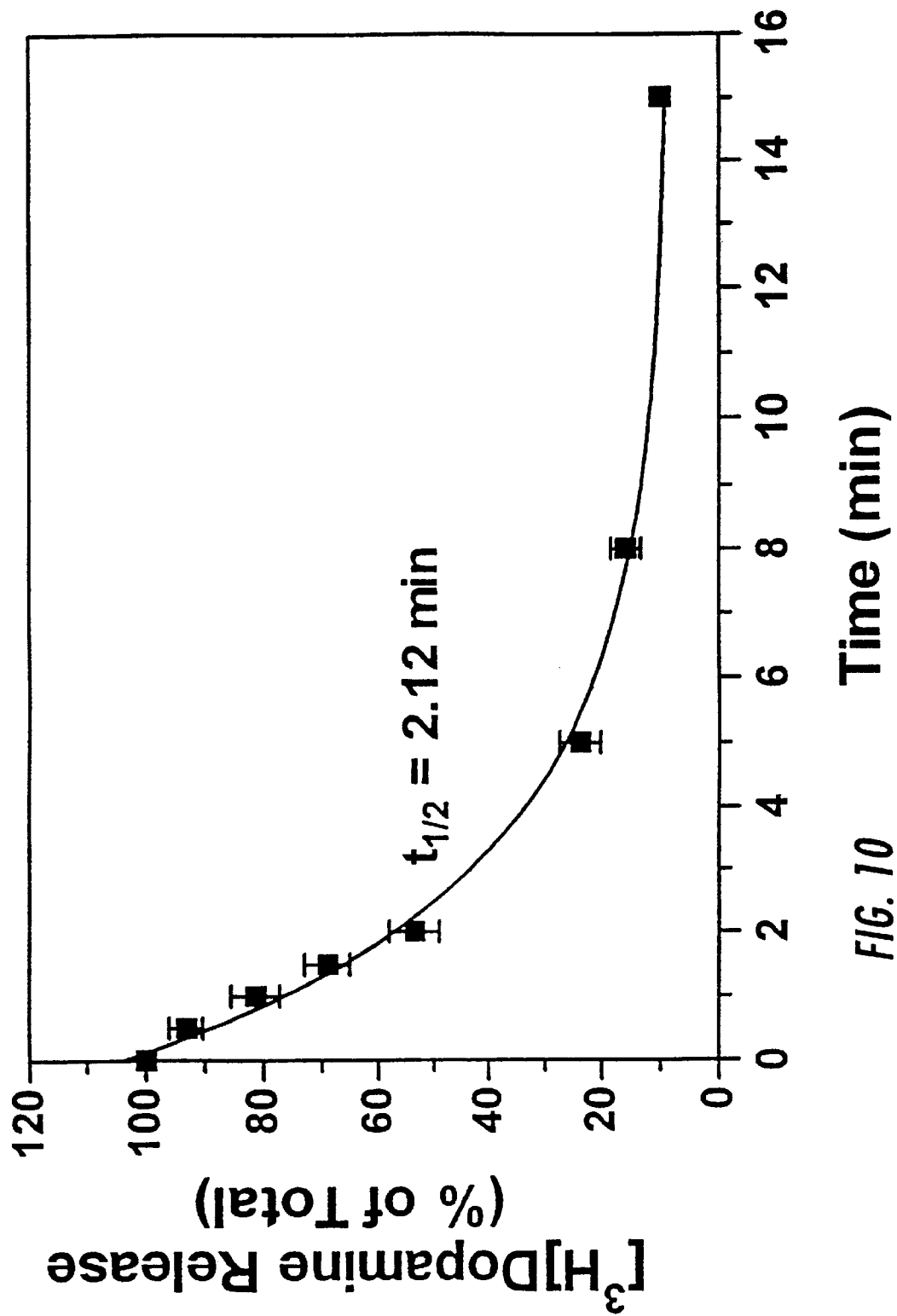

FIG. 10 shows the time course of spontaneous [$^3$H]DA efflux from [$^3$H]DA-preloaded striatal vesicles in the absence of drug. Data are expressed as mean±SEM [$^3$H]DA efflux as a percent of total [$^3$H]DA content of the vesicles at time 0. n4 experiments.

Figure 11:
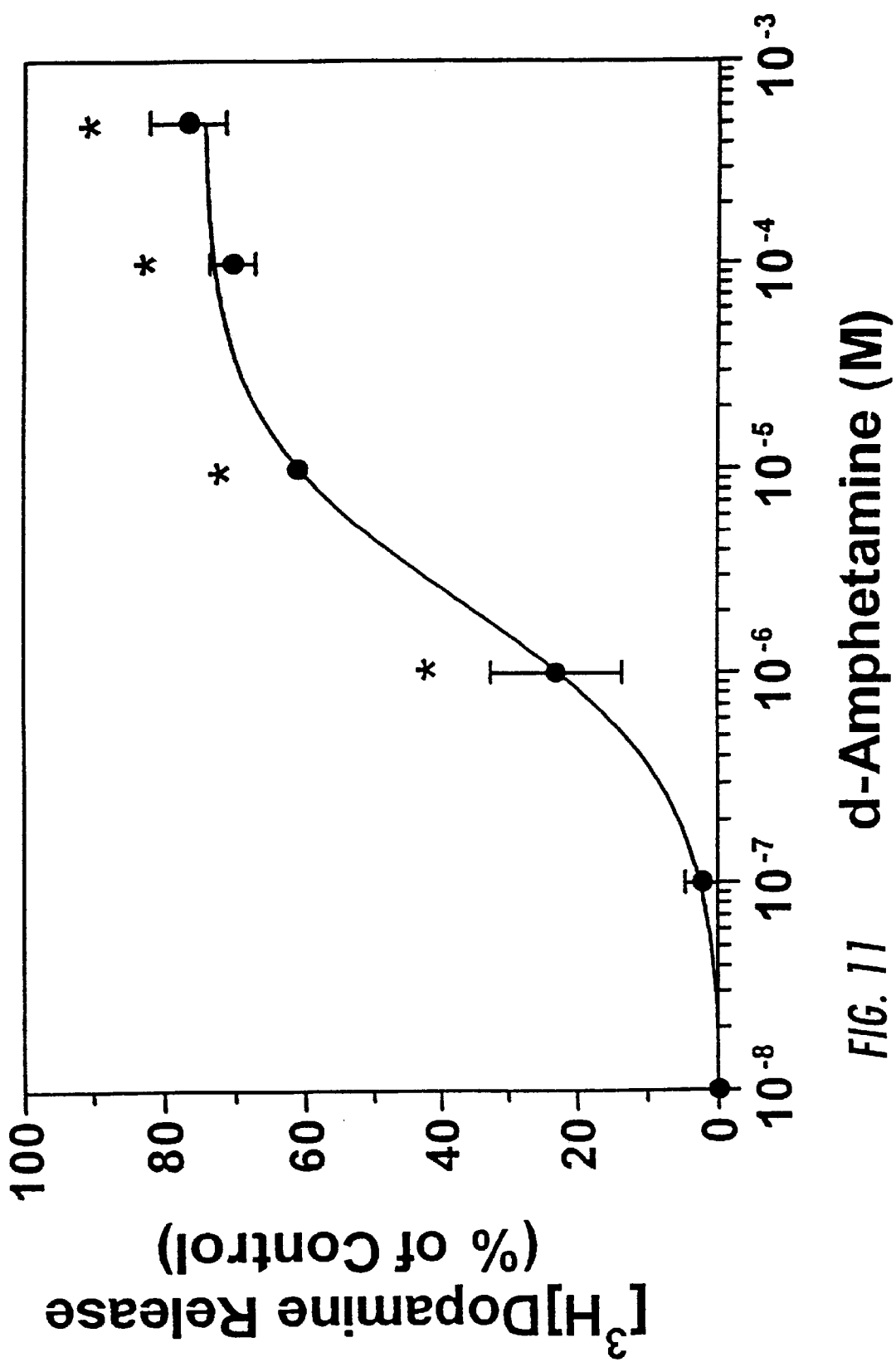

FIG. 11 shows that d-amphetamine evokes [$^3$H]DA release from synaptic vesicles preloaded with [$^3$H]DA. d-Amphetamine-evoked vesicular [$^3$H]DA release was expressed as percent of control content. The total amount of [$^3$H]DA present in control samples was 4.37±1.06 pmol/mg protein. *p<0.05, significantly different from control; Fisher least significant difference post hoc test. n3 experiments.

Figure 12:
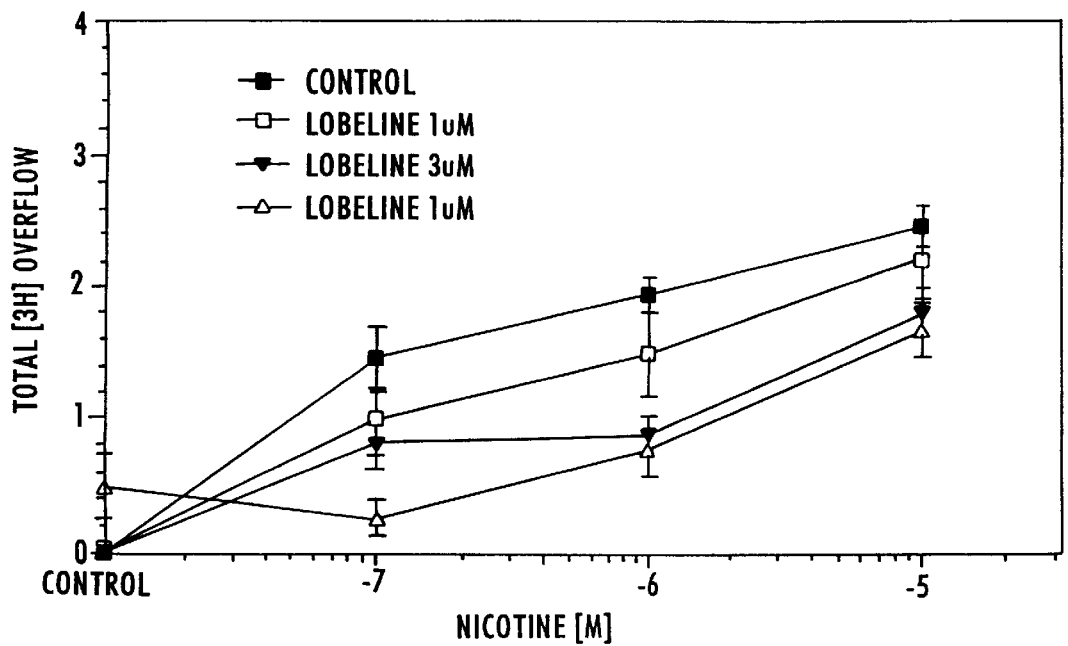

FIG. 12 depicts lobeline inhibition of nicotine-evoked [$^3$H]dopamine release from rat striatal slices. Striatal slices were obtained from rat brain, preincubated with [$^3$H] dopamine (0.1 $\mu$M) for 30 min and subsequently superfused with Kreb's buffer for 60 min. Following the initial period of superfusion, slices were superfused with buffer containing various concentrations of lobeline for 30 min and subsequently various concentrations of nicotine were included in the buffer. Superfusate samples were collected to determine the ability of lobeline to inhibit the nicotine-induced response.

Figure 13:
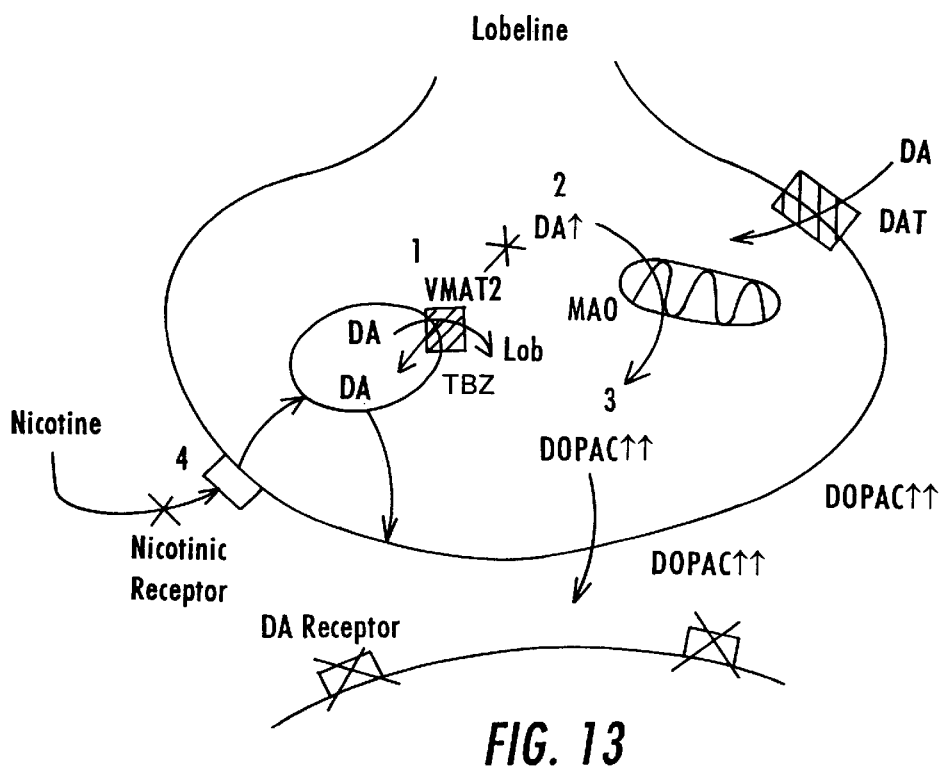

FIG. 13 illustrates the current understanding of the primary mechanism of the action of lobeline in the central nervous system.

DETAILED DESCRIPTION OF THE INVENTION

As used herein, the term "lobeline" refers to a compound having the general chemical formula 2-[G-($\beta$-hydroxyphenethyl)-1-methyl-2-piperidyl]-acetophenone. The term "lobeline" as used herein refers to the above compound in its free form, or as a salt thereof, which has the physiological activity addressed. Inasmuch as a compound having this formula has three chiral centers, eight optical isomers of the compound can exist. However, particular optical isomer(s) are not intended herein unless specifically mentioned.

The term "lobeline analogs" and equivalents thereof, as used herein, refers to chemical derivatives of lobeline, such as those obtained by oxidation or reduction of lobeline, others obtained by esterification of lobeline and its redox derivatives, as well as various substitutions at the N-position of the piperidinyl group in the lobeline molecule.

Preferred lobeline analogs, which may act as prodrugs of lobeline itself when metabolized by the body, include those contemplated by formula (I) (without regard to chirality):

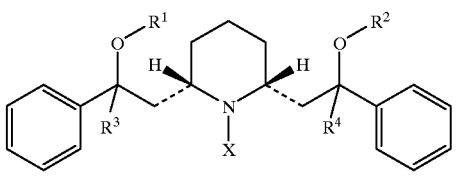

(I)

where $R^1$ and $R^2$ each independently represents hydrogen, lower alkyl, lower alkenyl, lower alkylcarbonyl, arylcarbonyl, e.g., phenylcarbonyl, aralkylcarbonyl, e.g., alkylphenylcarbonyl, lower alkoxycarbonyl, lower alkylaminocarbonyl, higher alkylcarbonyl, and poly (alkyleneoxide)carbonyl; $R^3$ and $R^4$ each independently represents hydrogen or combines with $R^1$ and $R^2$, respectively, to form a double bond; and X represents H or lower alkyl. Whenever a carbonyl-containing substituent is provided as $R^1$ or $R^2$, it is understood that the carbonyl group is covalently bonded to the respective O atom appearing in formula (I). Thus, in the instances where the substituent is an alkoxycarbonyl or alkylaminocarbonyl, a carbonate or carbamate linkage is present in the molecule.

Preferred substituents for $R^1$ and $R^2$ include methylcarbonyl (acetyl), phenylcarbonyl (benzoyl), natural fatty acid groups, e.g., palmitoyl, oleyl, linoleyl, stearyl, and lauryl, and polyethyleneglycol (PEG) covalently bonded to the molecule via a carbonate linkage. Long chain moieties such as a PEG group in a lobeline prodrug enhance transdermal delivery of the molecule, which may be metabolized to lobeline and derivatives thereof.

As used herein, the terms "lower alkyl", "lower alkenyl", "lower alkoxy", and the like, refer to normal, branched and cyclic hydrocarbyl groups containing 1 to 6 carbon atoms. The term "higher alkyl" includes alkyl groups containing 7 to about 20 carbon atoms. The term "aryl" refers to a hydrocarbon group containing one or more aromatic rings, optionally substituted with one or more heteroatoms. The term "aralkyl" refers to an aryl group covalently bonded to a lower alkyl group.

It is, of course, contemplated that certain lobeline analogs having the above formula may be converted into a different molecule upon metabolism by the body. For example, whenever an acetyl group is present at $R^1$ and/or $R^2$ in the compound, the acetyl group may be removed by metabolic processes, e.g., such as occur in the gastrointestinal tract or the liver. The choice of substituents is subject to considerations of toxicity, side effects, dosage, and the like.

Particularly preferred lobeline analogs are those in which (i) both $R^1$ and $R^2$ are H (i.e., a lobelanidine compound), (ii) either $R^1$ or $R^2$ is H and the other combines with $R^3$ or $R^4$ to form a double bond (i.e., a lobeline compound), and (iii) both $R^1$ and $R^2$ combine with either $R^3$ or $R^4$ to form a double bond (i.e., a lobelanine compound). It is also preferred that X in the above formula represents a methyl group. Preferably, the chirality at the 2 and 6 positions of the piperidyl ring of the compounds is the same as in naturally occurring lobeline.

Lobeline, as well as analogs thereof, can be administered in its free base form or as a soluble salt. Whenever it is desired to employ a salt of lobeline or analog, it is preferred that a soluble salt be employed. Some preferred salts include the hydrochloride, hydrobromide, nitrate, sulfate, tartrate, fumarate, citrate, maleate, ascorbate, lactate, aspartate, mesylate, benzene sulfonate, propionate and succinate salts. Also, other anionic moieties such as fatty acid salts can be used, e.g., palmitate salt.

As used herein, an "effective amount", and similar usages, refers to an amount of a drug effective to reduce an individual's desire for a drug of abuse, or for food.

A pharmaceutical composition containing a lobeline compound of the invention is also contemplated, which may include a conventional additive such as a stabilizer, buffer, salt, preservative, filler, flavor enhancer, and the like, as known to those skilled in the art. Representative buffers include phosphates, carbonates, citrates, and the like. Exemplary preservatives include EDTA, EGTA, BHA, BHT, and the like.

A composition of the invention may be administered by inhalation, i.e., intranasally as an aerosol or nasal formulation; topically, i.e., in the form of an ointment, cream or lotion; orally, i.e., in solid or liquid form (tablet, gelcap, time release capsule, powder, solution, or suspension in aqueous or non-aqueous liquid); intravenously as an infusion or injection, i.e., as a solution, suspension, or emulsion in a pharmaceutically acceptable carrier; transdermally, e.g., via a transdermal patch; rectally, as a suppository, and the like.

Generally, it is expected that a pharmacologically effective dose of a present compound will require its administration in an amount less than $1 \times 10^{-3}$ mg/kg of body weight per day. The amount to be administered depends to some extent on the lipophilicity of the specific compound selected, since it is expected that this property of the compound will cause it to partition into fatty deposits of the subject. The precise amount to be administered can be determined by the skilled practitioner in view of desired dosages, side effects, the medical history of the patient, and the like. It is anticipated that the compound will be administered in an amount ranging from about $1 \times 10^{-5}$ to about $1 \times 10^{-3}$ mg/kg/day.

The present study was performed to determine the involvement of nicotinic receptors in lobeline-evoked [$^3$H] overflow from rat striatal slices preloaded with [$^3$H]DA. The calcium-dependency of the effect of lobeline and the ability of mecamylamine to inhibit the lobeline response were determined. To assess the contribution of potential effects on DA uptake, the effect of nicotine and lobeline to inhibit [$^3$H]DA uptake into striatal synaptosomes and synaptic vesicle preparations was also determined. Based on the present results of the in vitro superfusion studies, striatal dopamine (DA) and dihydroxy phenylacetic acid (DOPAC) content were also determined after lobeline superfusion in vitro, and after lobeline administration in vivo.

Effect of Nicotine on Superfused Rat Striatal Slices Preloaded with [$^3$H]DA.

Figure 1A:
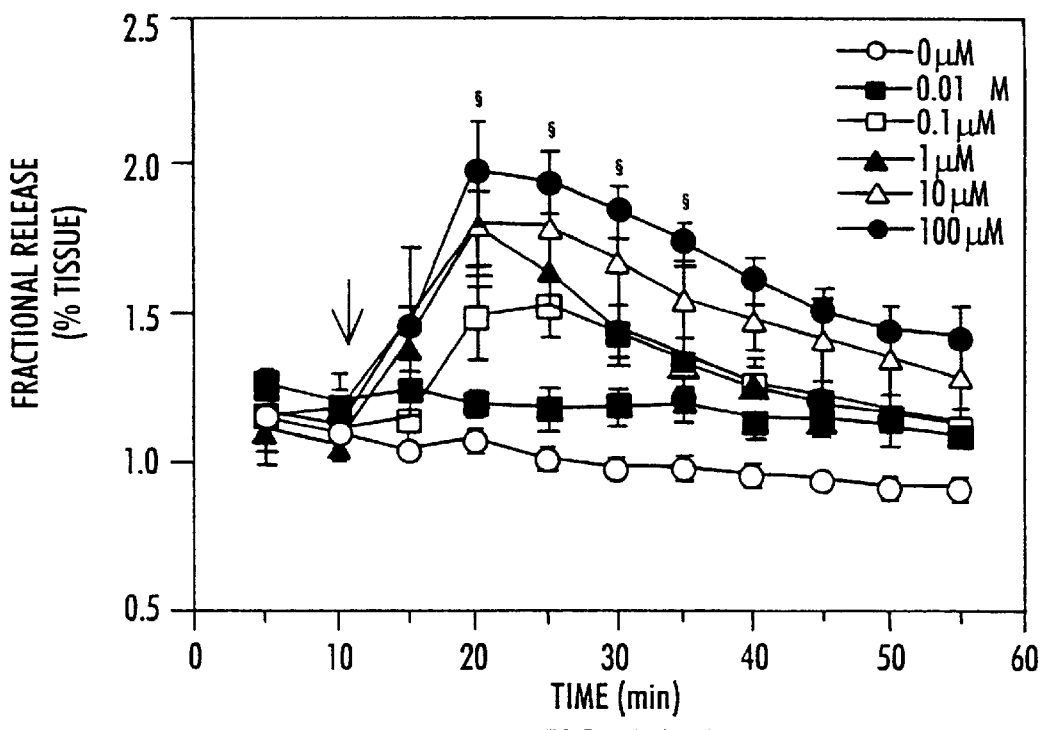
FIGS. 1A and 1B depict the time course of nicotine-evoked fractional release (A) and concentration-dependence of nicotine-evoked total [$^3$H]overflow (B) from rat striatal slices preloaded with [$^3$H]DA (3,4-dihydroxyphenylethyl-2-[N-$^3$H]-amine). Nicotine was added to the superfusion buffer after the second sample (as indicated by the arrow) and remained in the buffer until the end of the experiment. The data in FIG. 1A are presented as means±S.E. fractional release, which represents the tritium in the sample as a percentage of the total tritium in the slice at the time of sample collection. The data in FIG. 1B are presented as mean±S.E. total [$^3$H]overflow, which represents the area under the curve of the corresponding nicotine concentration-response as a function of time. §P<0.05, different from basal (5–10 min), when fractional release was collapsed across nicotine concentration; *P<0.05, significantly different from 0–0.01 μM and 1–100 μM; P<0.05, different from 0–0.1 μM and 100 μM; *P<0.05, different from 0–10 μM; Duncan's New Multiple Range Test. n=4–9 rats.

In a concentration-dependent manner, nicotine evoked an increase in the fractional release of tritium over the time course of the superfusion experiment (FIG. 1A). Repeated-measures, two-way ANOVA (analysis of variants) revealed a significant main effect of nicotine concentration ($F_{(8,429)}$=29.45, P<0.0001) and a significant main effect of time ($F_{10,429)}$=9.76, P<0.0001), but the concentration×time interaction was not significant ($F_{(80,420)}$=1.22, P>0.05). Fractional release peaked within 10–15 min after the addition of nicotine to the superfusion buffer. From 10–25 min after the addition of nicotine, fractional release was significantly increased above basal outflow, when the data were collapsed across nicotine concentration. At peak fractional release, the highest concentration of nicotine examined increased fractional release 2-fold above basal. Furthermore, when the data were collapsed across nicotine concentration, fractional release, from 30–45 min after nicotine addition, was not significantly different from basal, despite the presence of nicotine in the superfusion buffer throughout the superfusion period.

Figure 1B:
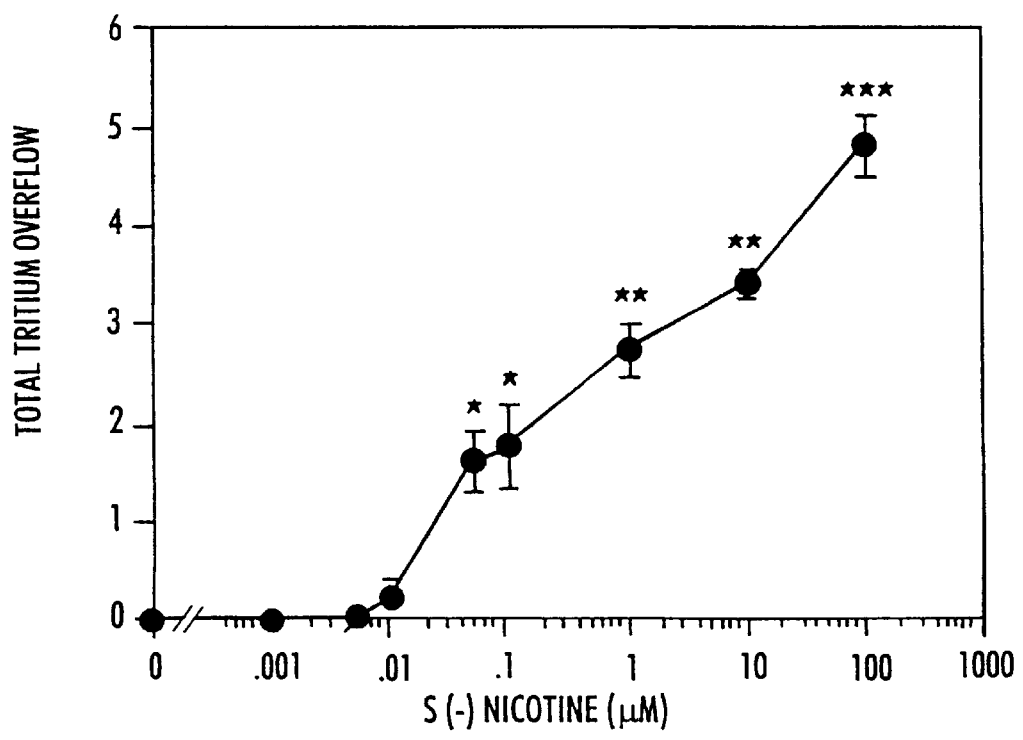

Presentation of the results as nicotine-evoked total [$^3$H] overflow accentuates the concentration-dependent nature of the response to nicotine (FIG. 1B). Repeated-measures, one-way ANOVA revealed a significant nicotine-concentration effect ($F_{(8,39)}$=25.77, P<0.0001). The lowest nicotine concentration which evoked a significant increase in [$^3$H]overflow was 0.05 μM. A plateau in the concentration-response curve was not apparent over the concentration range examined. Higher concentrations of nicotine were not examined because of the extensive work of Westfall and collaborators (Westfall, 1974; Westfall et al., 1987) indicating that nicotine concentrations higher than 100 μM act to release DA from superfused rat striatal slices by a mechanism which is not calcium-dependent nor nicotinic-receptor mediated.

Effect of Lobeline on Superfused Rat Striatal Slices Preloaded with [$^3$H]DA.

Figure 2A:
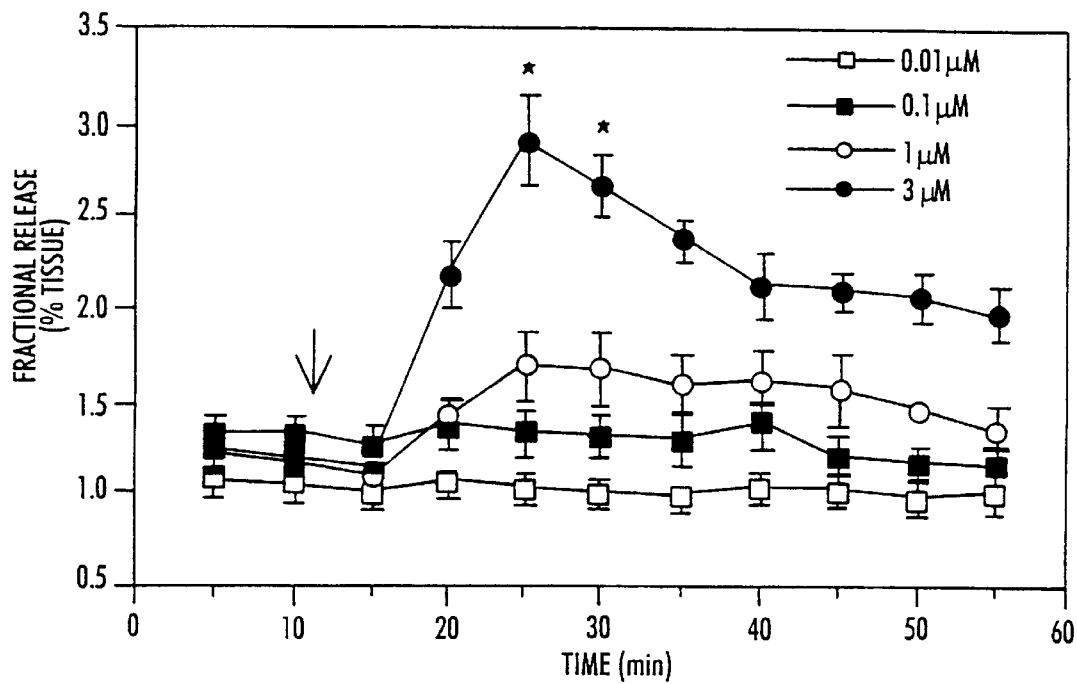
FIGS. 2A and 2B depict the time course of lobeline-evoked fractional release from rat striatal slices preloaded with [$^3$H]DA. Lobeline was added to the superfusion buffer after the collection of the second sample (as indicated by the arrow) and remained in the buffer until the end of the experiment. Data are presented as mean±S.E. fractional release, which represents the tritium in the superfusate sample as a percentage of the total tritium in the slice at the time of sample collection.

Lobeline evoked a marked concentration-dependent increase in fractional release of tritium over the time course of the superfusion experiment (FIG. 2). Repeated-measures, two-way ANOVA revealed a significant main effect of lobeline concentration ($F_{7,363}$=1057.13, P<0.0001), a significant main effect of time ($F_{10,363}$=132.24, P<0.0001) and a significant concentration×time interaction ($F_{(70,363)}$=44.85, P<0.0001). Low concentrations (0.01–1 μM) of lobeline did not significantly increase fractional release during the entire superfusion period. Lobeline (3 μM) evoked a significant increase in fractional release 15 and 20 min after its addiction to the buffer. Subsequently, the fractional release returned towards basal, despite the continuous presence of lobeline in the buffer. Fractional release evoked by high concentrations (10–100 μM) of lobeline was significantly increased 10 min after the addition of lobeline to the buffer and remained significantly higher than basal until the end of the experiment.

Figure 2B:
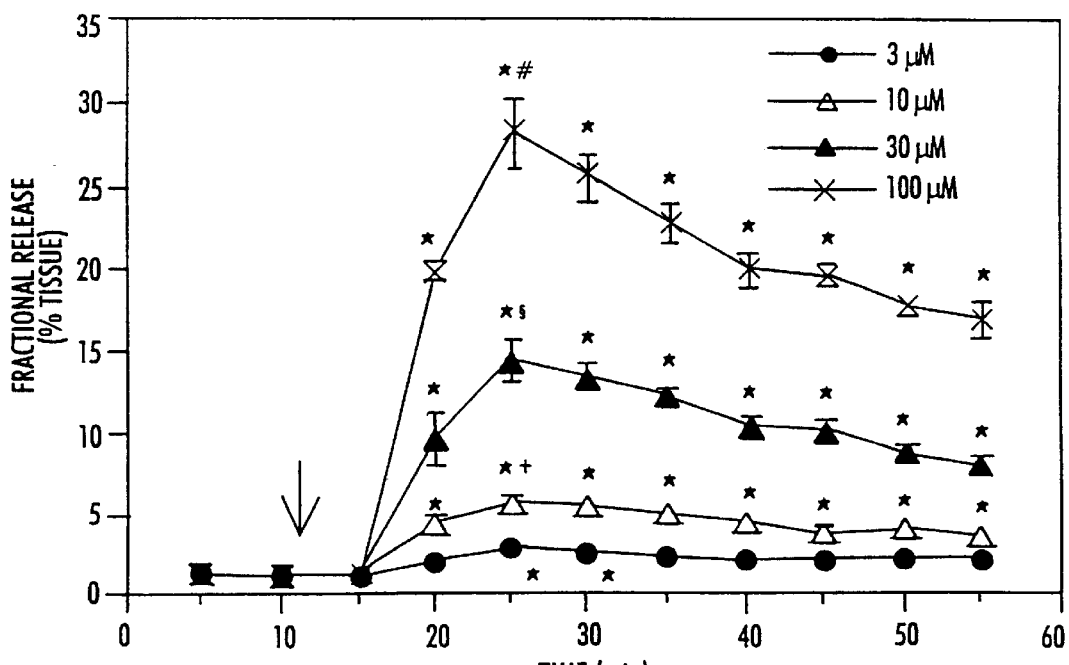

Of note is the magnitude of the response to lobeline in comparison to that observed after superfusion with nicotine. Peak fractional release after superfusion with 30 and 100 μM lobeline was approximately 15% and 30%, respectively, of the total tritium present in the striatal slice (FIG. 2B). Furthermore, over the remainder of the superfusion period, fractional release in superfusate samples continued to be 10–20% of the total tritium in the slice. On the other hand, peak fractional release induced by the highest concentration (100 μM) of nicotine was only 2% of total tritium in the slice, and fractional release returned to basal during the course of the experiment (FIG. 1A). These results suggest the potential for depletion of DA storage pools following superfusion with lobeline at high concentrations.

Expression of the results as total [$^3$H]overflow also revealed a concentration-dependent effect of lobeline and a marked increase in [$^3$H]overflow evoked by high concentrations of lobeline (FIG. 3). Repeated-measures, one-way ANOVA revealed a significant lobeline concentration effect ($F_{(6,35)}$=61.55, P<0.0001). The lowest concentration of lobeline to evoke a significant increase in total [$^3$H]overflow was 1 μM. As the lobeline concentration was increased, a significantly greater total [$^3$H]overflow was evoked. Furthermore, a plateau in the concentration-response curve was not apparent over the concentration range examined.

Lobeline-induced [$^3$H]overflow: Lack of Calcium-Dependency.

Previous studies (Westfall, 1974; Westfall et al., 1987) reported that nicotine (<100 μM)-evoked [$^3$H]overflow from rat striatal slices preloaded with [$^3$H]overflow was calcium-dependent. In order to determine if lobeline-induced [$^3$H] overflow was calcium-dependent, the effect of lobeline was determined in a calcium-free superfusion buffer containing 0.5 mM EGTA (ethylene glycol-bis(β-aminoethyl ether)-N, N,N',N'-tetraacetic acid (See Table 1). Two-way ANOVA revealed a significant main effect of lobeline concentration (within-group factor, $F_{(3,39)}$=473.08, P<0.001), however, the main effect of inclusion of calcium in the buffer was not significant (between-groups factor, $F_{(1,39)}$=0.13, P>0.05) and the interaction term also was not significant ($F_{(3,39)}$=1.64, P>0.05). Thus, the effect of lobeline on [$^3$H]overflow was not altered-following removal of calcium from the superfusion buffer.

TABLE 1

Lobeline Evokes [$^3$H] Overflow from Rat Striatal Slices Preloaded with [$^3$H] DA in a Calcium Independent Manner*

| Lobeline Concentration (μM) | Control Buffer | Calcium-Free Buffer |
|---|---|---|
| 0.1 | 0.6 ± 0.4 | 0 ± 0 |
| 1 | 2.0 ± 0.6 | 2.9 ± 0.2 |
| 10 | 31.9 ± 2.2 | 45.0 ± 4.2 |
| 100 | 198.0 ± 20 | 185.0 ± 12.0 |

*Concentration-response of lobeline was determined using either control Krebs' buffer or calcium-free buffer with the addition of 0.5 mM EGTA. Data are presented as mean ± S.E. total [$^3$H] overflow, n = 6 rats/group.

Nicotine-Evoked and Lobeline-Evoked [$^3$H]Overflow: Mecamylamine Antagonism.

In a concentration-dependent manner, mecamylamine significantly inhibited nicotine (10 μM)-evoked [$^3$H]overflow from rat striatal slices preloaded with [$^3$H]DA (See Table 2). Repeated-measures, one-way ANOVA revealed a significant mecamylamine concentration effect ($F_{(5,38)}$=4.46, P<0.005). Concentrations of mecamylamine from 0.1–100 μM inhibited (57%–5 91%) the effect of nicotine to evoke [$^3$H] overflow.

The time course of the effect of mecamylamine illustrates the pattern and the extent of the inhibition of the nicotine-evoked increase in fractional release (FIG. 4) Repeated-measures, two-way ANOVA revealed a significant main effect of mecamylamine concentration ($F_{(6,599)}$=19.59, P<0.0001), a significant main effect of time ($F_{(11,599)}$=4.98, P<0.0001), but the concentration×time interaction was not significant ($F_{(66,599)}$=0.97, P>0.05). When the data were collapsed across time, the lowest concentration of mecamylamine to produce a significant inhibition of nicotine's effect was 0.01 μM. The time course illustrates the small, but significant, inhibition (36%) of nicotine's effect produced by this low concentration of mecamylamine. Interestingly, the inhibitory effect of 0.01 μM mecamylamine was not detected when the results were expressed as total [$^3$H]overflow (See Table 2). The maximal inhibitory effect of the highest concentration (100 μM) of mecamylamine is also illustrated in FIG. 4 for comparison.

TABLE 2

Mecamylamine Inhibition of Nicotine(10 μM)-evoked [$^3$H] Overflow from Rat Striatal Slices Preloaded with [$^3$H] DA*

| Mecamylamine (μM) | Total [$^3$H] Overflow |
|---|---|
| 0 | 5.60 ± 1.20 |
| 0.01 | 3.57 ± 1.52 |
| 0.1 | 2.40 ± 0.87* |
| 1 | 1.59 ± 0.64** |
| 10 | 1.02 ± 0.43** |
| 100 | 0.54 ± 0.32** |

*Slices were superfused with buffer in the absence or presence of mecamylamine (0.01–100 μM)for 60 min, followed by 60 min superfusion with the addition of 10 μM of nicotine to the buffer containing the various concentrations of mecamylamine. Data are presented as mean ± S.E. total [$^3$H] overflow. Total [$^3$H] overflow for slices superfused in the absence of any drug was 0.06 ± 0.06. Slices superfused with nicotine (10 μM) in the absence of mecamylamine were considered control for statistical analysis. *P < 0.05, one-tailed, different from control; **P < 0.05, two-tailed, different from control; Dunnett's post hoc test. n = 8 rats.

The ability of mecamylamine (1–100 μM) to inhibit lobeline(0.1–100 μM)-evoked total [$^3$H]overflow is shown in Table 3. Concentrations of mecamylamine which significantly inhibited nicotine-evoked [$^3$H]overflow were utilized in these experiments. The effect of lobeline (0.1–100 μM) in the absence of mecamylamine represented control. Two-way ANOVA revealed a significant main effect of lobeline concentration (within groups factor, $F_{(4,56)}=603.84$, $P<0.0001$); however, both the main effect of mecamylamine concentration (between-groups factor, $F_{(3,14)}=2.79$, $P>0.05$) and the lobeline×mecamylamine interaction were not significant ($F_{(12,56)}=1.30$, $P>0.05$). Thus, lobeline-evoked [$^3$H]overflow was not inhibited by mecamylamine.

TABLE 3

Lobeline-evoked [$^3$H] Overflow from Rat Striatal Slices Preloaded with [$^3$H] DA is Not Inhibited by Mecamylamine*

| Mecamylamine Concentration ($\mu$M) | Lobeline Concentration ($\mu$M) | | | | |
|---|---|---|---|---|---|
| | 0.1 | 1 | 3 | 10 | 100 |
| 0 | 0.6 ± 0.4 | 2.0 ± 0.6 | 10.3 ± 0.8 | 31.9 ± 2.2 | 185.0 ± 12 |
| 1 | 0.9 ± 0.5 | 4.9 ± 1.8 | 10.8 ± 1.4 | 32.5 ± 1.0 | 180.0 ± 47.6 |
| 10 | 0.8 ± 0.3 | 2.4 ± 0.5 | 8.2 ± 1.5 | 41.0 ± 6.2 | 179.5 ± 12.2 |
| 100 | 0.5 ± 0.4 | 0.7 ± 0.1 | 6.5 ± 0.9 | 20.0 ± 2.0 | 160.4 ± 30.2 |

*Slices were superfused with buffer in the absence or presence of mecamylamine (1–100 $\mu$M) for 60 min, followed by 60 min superfusion with the addition of lobeline (0.1–100 $\mu$M) to the buffer. Data are presented as mean ± S.E. total [$^3$H] overflow. n = 4–6 rats.

The Effect of Nicotine and Lobeline on [$^3$H]DA Uptake Into Rat Striatal Synaptosomes and Synaptic Vesicles.

To determine if modulation of DA uptake contributed to the increase in [$^3$H]overflow evoked by nicotine or lobeline, [$^3$H]DA uptake into striatal synaptosomes and synaptic vesicles was determined (FIG. 5). Nicotine did not inhibit [$^3$H]DA uptake into striatal synaptosomes over the concentration range (0.001 nM–100 $\mu$M) examined. Before determining the effect of nicotine on synaptic vesicular [$^3$H]DA uptake, the purity of the isolated synaptic vesicle preparation was determined by electron microscopy of representative vesicle preparations. Plain spheroid or ellipsoid synaptic vesicle profiles of approximately 50 nm in diameter were the predominant membrane structures observed. Very few ($\leq 1$%) contaminating membrane fragments were present. The effect of nicotine on [$^3$H]DA uptake into synaptic vesicles was analyzed by repeated-measures, one-way ANOVA which revealed a significant nicotine concentration effect ($F_{9,28}=3.30$, $P<0.05$). However, Dunnett's post hoc analysis revealed that significant inhibition of uptake only occurred at very high concentration (1 mM) of nicotine.

Lobeline inhibited [$^3$H]DA uptake into synaptopsomes in a concentration-dependent manner (FIG. 5). Repeated-measures, one-way ANOVA revealed a significant lobeline concentration effect ($F_{9,38}=154.0$, $P<0.0001$). The lowest concentration of lobeline to produce a significant inhibition in the synaptosomal preparation was 30 $\mu$M. The $IC_{50}$ for lobeline to inhibit uptake into synaptosomes was 80±12 $\mu$M. Moreover, in contrast to nicotine, lobeline potently inhibited [$^3$H]DA uptake into synaptic vesicles in a concentration-dependent manner ($F_{8,26}=28.60$, $P<0.0001$). The lowest concentration of lobeline to produce a significant inhibition was 0.3 $\mu$M, and complete inhibition was obtained at 10 $\mu$M. The IC50 value for lobeline to inhibit vesicular uptake was 0.88±0.001 $\mu$M, which was 2-orders of magnitude lower than that for lobeline-induced inhibition of synaptosomal [$^3$H]DA uptake. Tetrabenazine (0.001–100 $\mu$M), a high affinity and specific inhibitor of the synaptic vesicular monoamine transporter (VMAT2), significantly inhibited striatal vesicular [$^3$H]DA uptake in a concentration-dependent manner ($F_{(9,28)}=23.78$, $P<0.0001$). The $IC_{50}$ for tetrabenazine was 77.7±1.3 nM, and the lowest concentration of tetrabenazine which significantly inhibited vesicular uptake was 0.07 $\mu$M. Complete inhibition was obtained at 1 $\mu$M tetrabenazine. Thus, lobeline was approximately one order of magnitude less potent than tetrabenazine in inhibiting vesicular [$^3$H]DA uptake.

Effect of Lobeline on Endogenous DA and DOPAC Content in Rat Striatum.

The marked increase in [$^3$H]overflow in response to superfusion with high concentrations of lobeline (FIGS. 2 and 3) and the lobeline-induced inhibition of synaptosomal and vesicular [$^3$H]DA uptake (FIG. 5) suggested that superfusion with lobeline may deplete striatal DA content. One-way ANOVA revealed a significant lobeline concentration effect on DA ($F_{(6,41)}=15.35$, $P<0.0001$) and DOPAC ($F_{(6,40)}=6.90$, $P<0.0001$) content in superfused striatal slices. Superfusion with low concentrations (0.1–10 $\mu$M) of lobeline did not alter DA or DOPAC content (data not shown); however, when slices were superfused with high lobeline concentrations (30–100 $\mu$M), lobeline significantly depleted endogenous DA content and increased DOPAC content compared to a control (FIG. 6).

To determine if lobeline-induced depletion of endogenous DA content occurred after in vivo administration of lobeline to rats, lobeline was administered (s.c.) acutely (0, 1, 3, 10, 30 mg/kg), intermittently (0, 3, 10 mg/kg, once daily for 10 days) or continuously (0, and 30 mg/kg, by osmotic minipump delivery for 21 days), and rat striata were obtained for the determination of endogenous DA and DOPAC content (See Table 4). Two-way ANOVA revealed that lobeline did not significantly alter either striatal DA ($F_{(4,58)}=0.05$, $P>0.05$) or DOPAC ($F_{(4,58)}=0.54$, $P>0.05$) content. Therefore, lobeline administration in vivo did not deplete striatal DA content at any dose of lobeline or any treatment regimen examined.

TABLE 4

In vivo Administration of Lobeline Does Not Alter DA and DOPAC Content in Rat Striatum*

| | Lobeline (mg/kg) | | | | |
|---|---|---|---|---|---|
| | 0 | 1 | 3 | 10 | 30 |
| DA | | | | | |
| Acute | 739 ± 64 | 756 ± 111 | 761 ± 103 | 841 ± 76 | 665 ± 126 |
| Intermittent | 743 ± 57 | ND | 778 ± 27 | 800 ± 41 | ND |
| Chronic | 840 ± 72 | ND | ND | ND | 856 ± 144 |
| DOPAC | | | | | |
| Acute | 84 ± 12 | 81 ± 12 | 89 ± 15 | 82 ± 8 | 72 ± 10 |
| Intermittent | 63 ± 6 | ND | 57 ± 12 | 57 ± 3 | ND |
| Chronic | 61 ± 4 | ND | ND | ND | 62 ± 10 |

*Rat striata were obtained 1 hr after acute lobeline administration (0, 1–30 mg/kg, s.c.); after intermittent lobeline administration (0,3 and 10 mg/kg, once daily injection for 10 days, s.c.); and after chronic lobeline delivery by osmotic minipump (0 and 30 mg/kg/day for 21 days, s.c.). Data are presented as mean ± S.E. ng/mg protein. ND: not determined. n = 6–8 rats/group.

[$^3$H]DTBZ Binding

Equilibrium binding analysis was performed to determine the values of $K_D$ and $B_{max}$ for [$^3$H]DTBZ binding to rat striatal vesicle membranes. Results revealed that the specific binding of [$^3$H]DTBZ was saturable and represented 60–80% of total binding of all [$^3$H]DTBZ concentrations (0.5–10 nM) examined (FIG. 7). Specific [$^3$H]DTBZ binding reached a plateau at a concentration of 3 nM. Nonspecific binding increased linearly as a concentration of [$^3$H]DTBZ increased. Scatchard analysis of the specific [$^3$H]DTBZ binding revealed a $K_D$ of 1.67 nM and a $B_{max}$ of 8.68 pmol/mg protein (FIG. 7, inset). The $K_D$ and $B_{max}$ values found in the present study are consistent with reported values obtained using mouse, rat, and human striatal synaptic vesicles (Scherman, 1986; Scherman et al., 1988).

Based on the Scatchard analysis, a 2 nM concentration approximating the $K_D$ value of [$^3$H]DTBZ was chosen to study the ability of lobeline and d-amphetamine to inhibit [$^3$H]DTBZ binding. Lobeline inhibited [$^3$H]DTBZ binding in a concentration-dependent manner ($F_{8,34}=15.4$, $p<0.0001$) (FIG. 8). The $IC_{50}$ value for lobeline to inhibit [$^3$H]DTBZ binding was 0.90±0.02 $\mu$M. The lowest concentration of lobeline to significantly inhibit [$^3$H]DTBZ binding was 0.3 $\mu$M. d-Amphetamine also inhibited [$^3$H]DTBZ binding in a concentration-dependent manner ($F_{8,31}=15.3$, $p<0.0001$) (FIG. 9). The $IC_{50}$ value for d-amphetamine to inhibit [$^3$H]DTBZ binding was 39.4±0.18 $\mu$M. The lowest concentration of d-amphetamine to significantly inhibit [$^3$H]DTBZ binding was 10 $\mu$M.

[$^3$H]DA Release From Striatal Vesicles

FIG. 10 illustrates the time course of spontaneous [$^3$H]DA efflux from the vesicles in the absence of drug. Time-effect curves fit a model of one-phase decay, and the $t_{1/2}$ was determined to be 2.12±0.21 min. The preparation of synaptic vesicles resulted in a preparation of 99% purity with absence of mitochondria. Thus, potential mitochondrial metabolism of [$^3$H]DA was eliminated, and the tritium measured in the vesicular [$^3$H]DA release assay represented [$^3$H]DA rather than [$^3$H]DA metabolites.

The ability of lobeline and d-amphetamine to evoke [$^3$H]DA release from synaptic vesicles preloaded with [$^3$H]DA was determined at 8 min, at which time spontaneous [$^3$H]DA efflux had stabilized. Lobeline evoked [$^3$H]DA release from synaptic vesicles in a concentration-dependent manner ($F_{6,13}=6.24$, $p<0.0001$) (FIG. 3). The $EC_{50}$ value for lobeline to evoke [$^3$H]DA release from synaptic vesicles was 25.3±0.27 $\mu$M. The lowest concentration of lobeline to evoke [$^3$H]DA release from vesicles was 10 $\mu$M. d-Amphetamine also evoked vesicular [$^3$H]DA release in a concentration-dependent manner ($F_{5,13}=19.98$, $p<0.0001$) (FIG. 11). The $EC_{50}$ value for d-amphetamine to evoke [$^3$H]DA release from vesicles was 2.22±0.13 $\mu$M. The lowest concentration of d-amphetamine to evoke [$^3$H]DA release from synaptic vesicles was 1 $\mu$M.

To determine the effect of lobeline and d-amphetamine on the kinetics of [$^3$H]DA efflux, the effect of concentrations of lobeline and d-amphetamine that were 10 times the $EC_{50}$ were determined. Both lobeline and d-amphetamine significantly ($F_{2,9}=6.56$, $p<0.05$) decreased the $t_{1/2}$ (1.58±0.09 and 1.48±0.05 min, respectively) compared with control.

As shown in FIG. 12, lobeline inhibits nicotine-evoked DA release in a concentration-dependent manner. Rat striatal slices preloaded with tritium-labeled dopamine were treated first with various concentrations of lobeline and subsequently with various concentrations of nicotine. Lobeline inhibited nicotine-evoked DA release at low concentrations, e.g., 0.1–1 $\mu$M. This study establishes that lobeline competes effectively with nicotine at nicotinic receptors and should therefore be considered a nicotinic antagonist.

Current understandings of the action of lobeline in view of the present results are summarized in FIG. 13. Thus, lobeline (LOB) inhibits DA uptake into synaptic vesicles via VMAT2 (#1), resulting in a corresponding redistribution of presynaptic DA storage with an increase in the cytosolic DA pool (#2), and ultimately an increase in DOPAC production as a result of metabolism of the cytosolic DA pool by monoamine oxidase (MAO) (#3). Lobeline also binds to the nicotinic receptor sites (illustrated presynaptically on the dopaminergic terminal) and blocks this receptor and thereby inhibiting nicotine-induced activation of this receptor, diminishing the dopamine release from the terminal (#4).

The foregoing outline of lobeline's action suggests its use as a therapeutic agent in the treatment of schizophrenia, which has been characterized as an overactivity of dopamine systems. By releasing the vesicular dopamine pool into the cytoplasm where it can be metabolized lobeline functionally acts as a dopamine system antagonist and should be beneficial in treating schizophrenia.

Nicotine and its analogs are presently being investigated as therapeutic agents in the treatment of several diseases and pathologies, and have shown promise in this regard. These include cognitive disorders, head or brain trauma, memory loss, psychosis, sleep disorders, obsessive-compulsive disorders, panic disorders, myasthenia gravis, Parkinson's disease, Alzheimer's disease, Tourette's syndrome, Huntington's disease, and attention deficit disorder, and related conditions. However, nicotine activates and rapidly desensitizes its receptor sites, which results in inactivated receptors and functional antagonism of its further action. Since lobeline acts to antagonize nicotinic receptors directly, its potential as a therapeutic agent in treating these conditions is indicated.

The invention will now be discussed by way of certain examples, which illustrate, but do not limit, the invention.

EXAMPLES

Materials.

S(−)Nicotine ditartrate, nomifensine maleate, mecamylamine hydrochloride, and GBR 12909 were purchased from Research Biochemicals, Inc. (Natick, Mass.). Tetrabenazine was purchased from Fluka Chemika-BioChemika (Ronkonkoma, N.Y.). [$^3$H]Dopamine ([$^3$H]DA; 3,4-dihydroxyphenylethyl(2-[N-$^3$H])amine; specific activity, 25.6 Ci/mmol) was purchased from New England Nuclear (Boston, Mass.). Dopamine hydrochloride, 3,4-dihydroxyphenylacetic acid (DOPAC), 3,4-dihydroxybenzylamine hydrobromide (DHBA), lobeline hemisulfate, pargyline hydrochloride, HEPES (N-[2-hydroxyethyl piperazine]-N'-[2-ethanesulfonic acid]), potassium tartrate, adenosine 5'-triphosphate magnesium salt (ATP-Mg$^{2+}$), L(+)tartaric acid and 1-octanesulfonic acid sodium salt were purchased from Sigma Chemical Co. (St. Louis, Mo.). α-D-Glucose and sucrose were purchased from Aldrich Chemical Co., Inc. (Milwaukee, Wis.). Ascorbic acid was purchased from AnalaR (BHD Ltd., Poole, U.K.). Glutaraldehyde, osmium tetroxide and copper grids were purchased from EMS Inc. (Fort Washington, Calif.). Eponate 12 was purchased from Ted Pella, Inc. (Redding, Calif.). TS-2 tissue solubilizer was purchased from Research Products International (Mount Prospect, Ill.). Acetonitrile (HPLC grade) was purchased from EM Science (EM Industries, N.J.). All other chemicals were purchased from Fisher Scientific (Pittsburgh, Pa.).

Subjects.

Male Sprague-Dawley rats (200–250 g) were obtained from Harlan Laboratories (Indianapolis, Ind.) and were housed two per cage with free access to food and water in the Division of Lab Animal Resources at the College of Pharmacy at the University of Kentucky. Experimental protocols involving the animals were in strict accordance with the NIH *Guide for the Care and Use of Laboratory Animals* and were approved by the Institutional Animal Care and Use Committee at the University of Kentucky.

Example 1
In Vivo Administration of Lobeline.

For acute administration studies, lobeline (1, 3, 10 and 30 mg/kg) or vehicle (distilled water) was administered subcutaneously (s.c.) acutely, and striata were obtained 1 hr after injection for determination of endogenous DA and DOPAC content. For intermittent chronic administration studies, lobeline (3 and 10 mg/kg) or vehicle was administered s.c. once daily for 10 days. Rats were killed 24 hrs after the last injection and striata were obtained immediately for determination of endogenous DA and DOPAC content. For continuous chronic administration, an osmotic minipump (ALZET 2 mL4 model, ALZA Corporation, Palo Alto, Calif.) containing 152 mg/mL of lobeline was implanted s.c. under ether anesthesia. A flow rate of 2.5 $\mu$L/hr delivered lobeline (30 mg/kg/day) or vehicle continuously for a 21-day period. Striata were obtained for endogenous DA and DOPAC content determination 21 days after osmotic minipump implantation. Lobeline dose was expressed in terms of mg of lobeline hemisulfate salt per kg body weight.

Example 2
[$^3$H]DA Release Assay.

The effect of lobeline and nicotine on [$^3$H]overflow from rat striatal slices preloaded with [$^3$H]DA was determined using a previously published method (Dwoskin and Zahniser, 1986). Rat striata were rapidly dissected on ice and were sliced using a McIlwain tissue chopper. Slices (500 $\mu$m, 6–8 mg) were incubated in Krebs' buffer (in mM; 118 NaCl, 4.7 KCl, 1.2 $MgCl_2$, 1.0 $NaH_2PO_4$, 1.3 $CaCl_2$, 11.1 $\alpha$-D-glucose, 25 $NaHCO_3$, 0.11 L-ascorbic acid, and 0.004 EDTA (ethylenediamine tetraacetic acid), pH 7.4 and saturated with 95% $O_2$/5% $CO_2$) in a metabolic shaker at 34° C. for 30 min to allow for recovery of responsiveness. Slices were rinsed with 15 mL fresh buffer and then incubated in fresh buffer containing 0.1 $\mu$M [$^3$H]DA (6–8 slices/3 mL) for an additional 30 min. Subsequently, slices were rinsed with 15 mL fresh buffer and transferred to a glass superfusion chamber. Slices were superfused at 1 ml/min with Krebs' buffer (34° C., pH 7.4, aerated with 95% $O_2$/5% $CO_2$) containing nomifensine (10 $\mu$M), a DA uptake inhibitor, and pargyline (10 $\mu$M), a monoamine oxidase inhibitor, to ensure that [$^3$H]overflow primarily represented [$^3$H]DA, rather than [$^3$H]DA metabolites (Cubeddu et al., 1979; Zumstein et al., 1981; Rapier et al, 1988). After 60 min of superfusion when basal outflow was stabilized, two 5-min samples (5 mL) were collected to determine basal [$^3$H]outflow.

For the nicotine or lobeline concentration-response studies, a single concentration of either nicotine (0.001–100 $\mu$M) or lobeline (0.01–100 $\mu$M) was added to the superfusion buffer of individual chambers after the collection of the second basal sample, and the drug remained in the buffer for 60 min or until the end of experiment. Each chamber was exposed to only one concentration of nicotine or lobeline. The concentration-response for each drug was determined using a repeated-measures design. In each experiment, one slice from the same rat was superfused in the absence of drug and served as control To determine the calcium-dependency of the effect of lobeline, concentration-response experiments were performed as described above, however, slices were superfused in the absence of $CaCl_2$, and 0.5 mM EGTA was added to the superfusion buffer.

To determine the ability of mecamylamine to antagonize nicotine-evoked [$^3$H]overflow, a repeated-measure design was utilized also. Individual slices were superfused with a single concentration (0.01–100 $\mu$M) of mecamylamine for 60 min, followed by 60 min of superfusion with nicotine (10 $\mu$M) in the presence of the various mecamylamine concentrations. One slice in each experiment was superfused in the absence of mecamylamine to determine the effect of nicotine alone. A control slice was superfused with buffer alone. To determine the ability of mecamylamine to antagonize lobeline-evoked [$^3$H]overflow, a between-groups design was utilized. Slices were superfused for 60 min in the absence or presence of different concentrations (1–100 $\mu$M) of mecamylamine, a between-group factor, followed by superfusion for 60 min with a range of concentrations (0.1–100 $\mu$M) of lobeline, a within-group factor.

At the end of each experiment, each slice was solubilized with TS-2, and was incubated at room temperature overnight. The pH and volume of the solubilized tissue samples were adjusted to those of the superfusate samples. Radioactivity in the superfusate and tissue samples was determined by liquid scintillation counting (Packard model B1600 TR Scintillation Counter) with an efficiency of 59%.

Fractional release for each superfusate sample was calculated by dividing the tritium collected in each sample by the total tritium present in the tissue at the time of sample collection. Fractional release was expressed as a percentage of total tritium in the tissue at the time of sample collection. Basal outflow was calculated from the average of the tritium collected in the two 5-min samples just before the addition of drug. Nicotine or lobeline-evoked [$^3$H]overflow was calculated by summing the increases in collected tritium resulting from exposure to drug and subtracting the basal outflow for the equivalent period of drug exposure.

Example 3
Determination of Endogenous DA and DOPAC Content in Striatal Slices Following Superfusion with Lobeline.

To determine if lobeline exposure depleted endogenous DA content in the striatal slices, superfusion experiments were performed exactly as described above, except that slices were preloaded with 0.1 $\mu$M unlabeled DA, rather than the same concentration of [$^3$H]DA. At the end of the superfusion experiment, slices were processed in the endogenous DA and DOPAC content assay described below.

Example 4
Striatal DA and DOPAC Content Assay.

Striatal slices from superfusion experiments and striatal tissue from rats administered lobeline or vehicle in in vivo studies were assayed for endogenous DA and DOPAC content by a modification of a previously described method (Dubocovich and Zahniser, 1985). An aliquot (500 $\mu$L) of 0.1 M perchloric acid (pH 1.0) containing 0.14–0.29 $\mu$M 3,4-dihydroxybenzylamine hydrobromide (DHBA, internal standard) was added to 100 mg of striatum and the mixture was sonicated with an Ultrasonic Processor (40-Watt Model, Sonics & Materials, Danbury, Conn.). The homogenate was centrifuged at 30,000×g for 10 min at 4° C., and the supernatant was filtered (0.2 $\mu$m nylon membrane). An aliquot (50 $\mu$L) of the filtrate (1:1, 1:50, 1:100, 1:200 or 1:500 dilution with 0.1 M perchloric acid) was injected onto the high pressure liquid chromatograph with electrochemical detection (HPLC-EC) system. The HPLC-EC system consisted of syringe loading injector (Model 7725, Rheodyne L. P., Cotati, Calif.), Beckman Model 116 HPLC pump (Beckman, Fullerton, Calif.), ESA ODS ultrasphere C18 reverse-phase column (4.6 cm×75 mm, 3 micron particle size, ESA, Bedford, Mass.), and an ESA 5100A coulometric electrochemical detector with a model 5011 detector cell (E1=+0.05 V, E2=+0.32 V). The eluent was 6% acetonitrile, 10 $\mu$M EDTA, 1.4 mM 1-octane-sulfonic acid and 76 mM sodium phosphate monobasic (pH 3.1). All separations were performed at room temperature at a flow rate of 1 ml/min.

Complete separation of DA and DOPAC and reequilibration of the system required 9 min. The retention time of DA, DOPAC and DHBA standards was used to identify the relevant peak. Peak heights were used to calculate the detected amount of compound based on standard curves. The detection limit of DA and DOPAC was 0.2 and 0.05 pg/50 μL injected, respectively. Recovery of internal standard was routinely 75%.

Example 5

[$^3$H]DA Uptake Assay, Striatal Synaptosomal Preparation.

The uptake of [$^3$H]DA into striatal synaptosomes was determined using a modification of a previously published method (Masserano et al., 1994). The striata from a single rat were homogenized in 20 mL cold 0.32 M sucrose with 5 mM NaHCO$_3$ (pH 7.4) with 16 up and down strokes of a TEFLON pestle homogenizer (clearance approximately 0.003 inches). The homogenate was centrifuged at 2,000×g for 10 min at 4° C. The supernatant was centrifuged at 20,000×g for 15 min at 4° C. The pellet was resuspended in 2 mL assay buffer (in mM; 125 NaCl, 5 KCl, 1.5 MgSO$_4$, 1.25 CaCl$_2$, 1.5 KH$_2$PO$_4$, 10 α-D-glucose, 2 5 HEPES, 0.1 EDTA, 0.1 pargyline, 0.1 ascorbic acid, and saturated with 95% O$_2$/5% CO$_2$, pH 7.4). The final protein concentration was 400 μg/mL. The assay was performed in duplicate in a total volume of 500 μL. Aliquots (50 μL containing 20 μg of protein) were incubated with 50 μL of nicotine (final concentration 0.001 nM–100 μM) or 50 μL of lobeline (final concentration, 0.01–1000 μM) in a metabolic shaker at 34° C. for 10 min. Subsequently, a final DA ([$^3$H]DA/cold DA) concentration of 0.32 μM was added to each tube in a total volume of 66 μL, consisting of 16 μL of 0.01 μM [$^3$H]DA and 50 μL of 3 μM unlabelled DA. The incubation continued for 10 min at 34° C. The reaction was terminated by the addition of 3 mL cold assay buffer (without 1 mM catechol). Samples were rapidly filtered through a Whatman GF/B filter using a Brandel cell harvester (model MP-43 RS, Biochemical Research and Development Laboratories, Inc., Gaithersburg, Md.) and the filter was subsequently washed 3 times with 4 mL of cold assay buffer containing 1 mM catechol. Filters were previously soaked for 2 hrs in the cold assay buffer containing 1 mM catechol. Nonspecific uptake was determined in duplicate samples in the presence of 10 μM GBR 12909. Filters were placed into scintillation vials, 10 mL of scintillation cocktail was added and radioactivity was determined by scintillation spectrometry.

Example 6

Striatal Synaptic Vesicle Preparation.

The uptake of [$^3$H]DA into striatal synaptic vesicles was determined using previously published methods (Erickson et al., 1990). Striata from 3 rats were pooled and homogenized in 0.32 M sucrose (pH 7.5, 500 mg/14 mL) with 10 up and down strokes of a TEFLON pestle (clearance approximately 0.009 inches) over a 2 min period. The homogenate was then centrifuged at 2,000×g for 10 min at 4° C. and the resulting supernatant was centrifuged at 10,000×g for 30 min at 4° C. Synaptosomes (buffy coat) were separated from the underlying mitochondria and cellular debris (reddish pellet) by gentle swirling in 2 mL of 0.32 M sucrose. The enriched synaptosome fraction (2.0 mL) was subjected to osmotic shock by addition of 7 mL distilled H$_2$0 and was homogenized with 5 up and down strokes of the TEFLON pestle. The osmolarity was restored by the addition of 900 μL of 0.25 M HEPES and 900 μL of 1.0 M neutral potassium-tatrate buffer (pH 7.5) followed by a 20 min centrifugation (20,000×g at 4° C.). The supernatant was then centrifuged for 60 min (55,000×g at 4° C.). One mL of solution containing 10 mM MgSO$_4$, 0.25 M HEPES and 1.0 M potassium-tartrate buffer was added to the supernatant and the suspension was centrifuged (100,000×g for 45 min at 4° C.).

Example 7

[$^3$H]DA Uptake Assays Striatal Synaptic Vesicles.

Immediately before use, the final pellet was resuspended in the assay buffer (in mM; 25 HEPES, 100 potassium tartrate, 0.05 EGTA, 0.10 EDTA, 2 ATP-Mg$^{2+}$, 1.7 ascorbic acid, pH 7.4). Aliquots (160 μL containing 8–10 μg protein) of the resuspension were incubated with 20 μL of drug (nicotine, final concentration 0.001–1000 μM; lobeline, final concentration 0.001–100 μM; or tetrabenazine, final concentration 0.001–100 μM) and 20 μL of [$^3$H]DA (final concentration 0.3 μM) for 8 min at 37° C. in a total volume of 200 μL. The reaction was terminated by addition 2.5 mL of cold assay buffer containing 2 mM MgSO$_4$. Samples were rapidly filtered through Whatman GF/F filters using the Brandel cell harvester. The filters were then washed 3 times with 4 mL of cold assay buffer containing 2 mM MgSO$_4$. Filters were previously soaked in 0.5% polyethylenimine (PEI) solution for 2 hr at 4° C. Nonspecific uptake was determined by incubation of duplicate samples at 0° C. in the absence of drug. Filters were placed into scintillation vials, 10 mL of scintillation cocktail was added to each vial, and radioactivity was determined by scintillation spectrometry.

Example 8

[$^3$H]DTBZ binding.

[$^3$H]DTBZ binding was performed using a previously published method (Vincent and Near, 1991) with modifications. The final vesicle pellet from a pool of striata from three rats was resuspended in 6 mL of binding buffer (in mM; 24 HEPES, 100 L-(+)-tartaric acid dipotassium salt, 5 MgCl$_2$, 10 NaCl, 0.05 EGTA, 0.10 EDTA, 1.7 ascorbic acid, pH 7.4). For experiments determining the equilibrium of [$^3$H]DTBZ binding, aliquots (160 μL, 16 μg of protein/mL) of the vesicle resuspension were incubated in the absence or presence of [$^3$H]DTBZ (final concentration 0.5–10 nM) for 10 min at 25° C. in total volume of 500 μL. For experiments determining the inhibition of [$^3$H]DTBZ binding by lobeline or d-amphetamine, aliquots (160 μL, 15 μg of protein/mL) of the vesicle resuspension were incubated with lobeline (final concentration 0.01–1,000 μM) or d-amphetamine (final concentration 0.1–3,000 μM) and 2 nM [$^3$H]DTBZ for 10 min at 25° C. in total volume of 500 μL. The reaction was terminated by rapid filtration of the samples onto Whatman GF/F filters using the Brandel cell harvester. Nonspecific binding was determined using 20 μM TBZ. Filters were previously soaked for 2 h in ice-cold polyethylemmine (0.5%). After the filters were washed three times with the ice-cold buffer, they were placed into scintillation vials. Subsequently, 10 mL of scintillation cocktail was added to each vial, and radioactivity was determined by scintillation spectrometry.

Example 9

[$^3$H]DA release from striatal synaptic vesicles.

The final vesicle pellet from a pool of striata from three rats was resuspended in 3 mL of release assay buffer (in mM: 25 HEPES, 100 L-(+)-tartaric acid dipotassium salt, 0.05 EGTA, 0.10 EDTA, 2 Mg$^{2+}$-ATP, and 1.7 ascorbic acid, pH 7.4) and then incubated with [$^3$H]DA (0.3 μM) for 8 min at 37° C. The resuspension was centrifuged for 45 min (100, 000 g at 4° C.), and the resulting pellet was resuspended in 6 mL of release assay buffer. For the kinetic analysis of spontaneous [$^3$H]DA efflux, aliquots (160 μL) of the resuspension were incubated for eight time points from 0 to 15 min and the $t_{1/2}$ determined. [$^3$H]DA efflux represents the net result of events, i.e., release and reuptake. The concentration effect of lobeline and d-amphetamine to alter [$^3$H]DA release was determined at 8 min, at which time spontaneous [$^3$H]DA efflux had stabilized. Aliquots (160 μL) of the resuspension were incubated with lobeline (final concentration 0.01–300 μM) or d-amphetamine (final concentration 0.1–500 μM) for 8 min at 37° C. in a total volume of 200 μL. To determine the effect of lobeline and d-amphetamine on the kinetics of [$^3$H]DA efflux, concentrations of drug that were 10 times the $EC_{50}$ were utilized, and efflux was measured from 0 to 15 min to obtain the $t_{1/2}$ in the presence of drug. The reaction was terminated by addition of 2.5 mL of ice-cold assay buffer containing 2 mM $MgSO_4$. Samples were rapidly filtered through Whatman GF/F filters using the Brandel cell harvester. Filters were previously soaked for 2 h in ice-cold polyethylenimine (0.5%) and processed as described above in the [$^3$H]DTBZ binding assay.

The amount of drug-induced [$^3$H]DA release from synaptic vesicles was calculated by subtracting the amount of tritium remaining in the drug-exposed samples from that remaining in the control samples (in the absence of drug). The amount of drug-induced [$^3$H]DA release was then divided by the amount of tritium remaining in the control samples and was expressed as a percentage of control.

Example 10

Lobeline Inhibition of Nicotine-evoked Release of [$^3$H]DA from Rat Striata.

Studies of the effect of various concentrations of lobeline on nicotine-evoked release of tritium labeled dopamine from rat striata were performed as described above in Example 2. Striatal slices were superfused with buffer containing various concentrations of lobeline for 30 minutes and subsequently various concentrations of nicotine were included in the buffer.

Example 11

Electron Microscopy.

To confirm the purity of the isolated synaptic vesicles, vesicle pellets from rat striata were processed for electron microscopy. The pellet was fixed for 2 hr with 3.5% glutaraldehyde in 0.1 M phosphate buffer (pH 7.3). After a brief rinse in phosphate buffer, the pellet was postfixed for 2 hr in 1% osmium tetroxide in phosphate buffer. The pellet was then dehydrated five times in graded ethanol (50%, 70%, 80%, 90% and 100%), and embedded in Eponate 12 resin. Ultrathin (60–80 nm) sections were cut on an Ultracut E microtome (Reichert-Jung, Inc., Vienna, Austria) and were collected on copper grids. The sections were then stained with saturated uranyl acetate in 70% ethanol and 0.04 M lead citrate. The grids were viewed with a Hitachi H-7000 transmission electron microscope (Hitachi, Tokyo, Japan).

Example 12

Statistics.

Repeated-measures, one-way ANOVA was performed to analyze the results of the following experiments: the concentration effect of nicotine or lobeline on [$^3$H]overflow, the ability of mecamylamine to antagonize nicotine (10 μM)-evoked [$^3$H]overflow, and the effect of lobeline on DA and DOPAC content in striatal slices. Two-way ANOVAs were used to analyze the concentration effect of lobeline or nicotine on the time course of fractional release, to analyze the calcium-dependency of lobeline-evoked [$^3$H]overflow and to analyze mecamylamine antagonism of lobeline-evoked [$^3$H]overflow. Inhibition of synaptosomal and vesicular [$^3$H]DA uptake were analyzed by repeated-measures, one-way ANOVA, and by an iterative nonlinear least-squares curve-fitting program (GraphPAD-PRIZM; GraphPAD, San Diego, Calif.) to obtain $IC_{50}$ values. Dunnett's post hoc test was used to compare treatment means to a single control mean. Also, Duncan's New Multiple Range Test or Fisher's LSD post hoc analysis were used to compare pairs of treatment means. Duncan's New Multiple Range Test was used when significant one-way ANOVA's were obtained or when significant main effects were obtained in the two-way ANOVA's. Fisher's LSD post hoc analysis is a more conservative test, which takes into account error which cumulates during multiple comparisons of pairs of means. Fisher's LSD analysis was used when the interaction term was significant in the two-way ANOVAs, specifically in the post hoc analysis of drug×time interactions. Statistical significance was reached when P<0.05 (two-tailed, unless otherwise indicated).

Concentration-response and kinetic data were analyzed by repeated-measures one-way ANOVA and between-group one-way ANOVA, respectively. When appropriate, Fisher's least significant difference post hoc test was used to determine significant differences between treatment means. $IC_{50}$ and $EC_{50}$ values were obtained by an iterative nonlinear least-squares curve-fitting program (GraphPAD-PRIZM: GraphPAD, San Diego, Calif., U.S.A.) for one-site competition and sigmoidal concentration response, respectively. The $t_{1/2}$ was obtained by an iterative nonlinear least-squares curve-fitting program for one-phase decay. $K_D$ and $B_{max}$ values were obtained by Scatchard analysis using an iterative linear least-squares curve-fitting program.

Conclusion

The results of the present study demonstrate that lobeline weakly evokes [$^3$H]overflow from rat striatal slices preloaded with [$^3$H]DA in a concentration-dependent manner. However, in contrast to nicotine, lobeline-evoked [$^3$H] overflow is calcium-independent and mecamylamine-insensitive. Although lobeline has previously been considered a nicotinic agonist, the present results suggest that lobeline acts to evoke [$^3$H]overflow via a mechanism other than by stimulation of nicotinic receptors. The present results, coupled with the fact that lobeline binds to nicotinic receptors with high affinity [Lippiello, 1986; Brousolle et al., 1989), further suggest that lobeline actually is a nicotinic antagonist.

Similar to nicotine, lobeline evoked [$^3$H]overflow from [$^3$H]DA-preloaded striatal slices in a concentration-dependent manner. However, as illustrated by the time course (FIG. 2) and the concentration-response curve (FIG. 3), the pattern and the magnitude of the effect of lobeline was different from that of nicotine. The peak effect occurred 10–20 min following the start of lobeline exposure and, at least at the low concentrations, the response returned to basal levels despite continued superfusion with lobeline. However, the response remained significantly above basal levels during superfusion with the higher lobeline concentrations (30–100 μM). Moreover, the effect of lobeline on [$^3$H]overflow was markedly increased (8–34 fold) compared to the effect of nicotine, particularly at the higher concentrations (10–100 μM) examined (FIGS. 1B and 3). Additionally, a depletion of endogenous DA and an increase in endogenous DOPAC was observed in the striatal slices superfused with these high concentrations of lobeline, indicative of marked DA utilization in response to lobeline, and potential toxicity, at least in vitro (FIG. 6). Furthermore, in contrast to nicotine, the effect of lobeline was found in the present study to be calcium-independent and not inhibited by mecamylamine. Thus, despite the reported high affinity of lobeline for the [$^3$H]nicotine binding site, lobeline evidently evokes [$^3$H]overflow from rat striatal slices preloaded with [$^3$H]DA by a mechanism other than stimulation of nicotinic receptors.

The present results further demonstrate that, in contrast to nicotine, lobeline potently inhibits [$^3$H]DA uptake into striatal synaptosomes and vesicles. Significant inhibition of [$^3$H]DA uptake into synaptic vesicles was observed at a low concentration of 0.3 µM of lobeline, and the $IC_{50}$ for this effect was 0.88 µM (FIG. 5). Additionally, at higher concentrations ($\geq$30 µM), [$^3$H]DA uptake into striatal synaptosomes was also significantly inhibited. The $IC_{50}$ for lobeline-induced inhibition of synaptosomal uptake was 80 µM, i.e., two orders of magnitude higher than that for inhibition of uptake into synaptic vesicles. The present results from the synaptosomal assay are in good agreement with a previous report of lobeline-induced inhibition of [$^3$H]DA uptake into mouse striatal synaptosomes (Debler et al., 1988).

In the present study, nicotine only inhibited vesicular [$^3$H]DA uptake at a very high concentration (~1 mM) and no inhibition of synaptosomal [$^3$H]DA uptake was observed. The lack of effect of nicotine to inhibit DA uptake into striatal synaptosomes is in agreement with previous reports (Kramer et al, 1989; Izenwasser et al., 1991; Rowell and Hill, 1993).

The results of the present study indicate that the synaptic vesicular DA (SVDA) transporter is significantly more sensitive to lobeline-induced inhibition than the plasma membrane DA transporter, and that both transport processes are not modulated to any great extent by nicotine. Since these two transporters are structurally and functionally different (see review, Brownstein and Hoffman, 1994), it is not surprising that they are differentially sensitive to inhibition by lobeline.

The lobeline-induced increase in DA concentration in the extracellular space (as reflected by an increase in [$^3$H] overflow in superfusate in the [$^3$H]DA release assay) is consistent with the lobeline-induced inhibition of vesicular and synaptosomal DA uptake. Notably, the lowest concentration of lobeline to significantly evoke [$^3$H]overflow in the superfusion assay was 1 µM, which is within the range of concentrations observed to specifically inhibit vesicular DA uptake, since higher concentrations (i.e. >30 µM) were required to detect the inhibition of synaptosomal DA uptake. The observation that the lobeline-induced [$^3$H]overflow is not calcium-dependent suggests that the released DA originated from cytosolic rather than vesicular pools. Since lobeline is a very lipophilic compound (Barlow and Johnson, 1989; Reavill et al, 1990; Bhat et al., 1991), it could easily gain access to the vesicular transporter by passive entrance into the neuron and its vesicles. Lobeline-induced inhibition of vesicular DA uptake could occur via two mechanisms, dissipation of the vesicle proton gradients and/or interaction with a substrate site on the vesicular transporter. Because lobeline is a weak base, and as a result of the lower pH inside the vesicle, lobeline could accumulate in synaptic vesicles in its charged form (i.e. protonated). Once lobeline exceeded the buffering capacity within the vesicle, the vesicular pH gradient would be attenuated with a resulting decrease in available energy for DA uptake (Beers et al., 1986; Johnson, 1988). Subsequently, uncharged DA would diffuse out of the vesicles in accordance with the concentration gradient, such that DA concentrations in the cytosol would increase. Elevation of cytosolic DA would promote reverse transport and DA release from the presynaptic terminal into the extracellular space. Furthermore, neurotoxicity may result from the increased cytosolic DA, which could likely undergo auto-oxidation and enzymatic oxidative metabolism, leading to the increased formation of DOPAC, hydrogen peroxide, free radicals, and active quinones (Graham et al., 1978; Slivka and Cohen, 1985). Thus, lobeline-induced redistribution of intracellular DA within the presynaptic terminal would result in DA release and potential neurotoxicity.

Taken together, lobeline appears to act in an amphetamine-like manner as a DA releasing agent. Amphetamine is lipophilic, entering neurons by passive diffusion (Ross and Renyi, 1966; Fischer and Cho, 1989; Liang and Rutledge, 1982). At low concentrations, amphetamine enters neurons via the DA transporter; and as a result, DA is released into the extracellular space by carrier-mediated exchange diffusion (Fischer and Cho, 1979; Liang and Rutledge, 1982), a calcium-independent mechanism which is sensitive to DA uptake inhibitors (Hurd and Ungerstedt, 1989; Parker and Cubeddu, 1986; Zaczek et al., 1991; Levi and Raiteri, 1993). Furthermore, amphetamine is a weak base which has been reported to interact with the vesicular substrate site (Schuldiner et al, 1993; Gonzalez et al., 1994), to enter synaptic vesicles, and dissipate the vesicular proton gradient resulting in intracellular redistribution and subsequent release of neurotransmitter (Knepper et al., 1988; Sulzer and Rayport, 1990; Sulzer et al., 1995). In comparison with amphetamine, few studies have focused on the mechanism of action of lobeline; however, the present findings indicate many similarities in the action of these two drugs, even though lobeline has often been categorized as a nicotinic agonist (Decker et al, 1995).

Results from the present study demonstrate that lobeline potently inhibits [$^3$H]DTBZ binding to synaptic vesicle membranes from rat striatum. The potency for lobeline to inhibit [$^3$H]DTBZ binding is consistent with that previously reported for lobeline to inhibit [$^3$H]DA uptake into synaptic vesicles. These results suggest that lobeline specifically interacts with the DTBZ sites on VMAT2 to inhibit DA uptake into synaptic vesicles. Furthermore, in the present study, lobeline was observed to evoke [$^3$H]DA release from [$^3$H]DA-preloaded synaptic vesicles.

Moreover, lobeline inhibited vesicular [$^3$H]DA uptake 28-fold more potently than it evoked [$^3$H]DA release from the vesicles. Inherent in the release methodology, the observed lobeline-evoked [$^3$H]DA release could involve two processes, i.e., stimulation of release and inhibition of reuptake. However, based on the observed rapid kinetics of the [$^3$H]DA efflux from the vesicle preparation in the absence of drug, the influence of uptake as a component process of release is likely to be small or insignificant.

In contrast to lobeline, d-amphetamine was found to evoke [$^3$H]DA release from the [$^3$H]DA-preloaded synaptic vesicles 18-fold more potently than it inhibited [$^3$H]DTBZ binding to synaptic vesicle membranes. Furthermore, d-amphetamine has been reported to inhibit [$^3$H]DTBZ binding to vesicle membranes with a potency ~1 to 2 orders of magnitude less than that reported for its inhibition of the uptake of monoamines (Philippu and Beyer, 1973; Ary and Komiskey, 1980; Erickson et al., 1996; present results). Taken together, these results suggest that d-amphetamine interacts with a different site than lobeline on VMAT2 to inhibit monoamine uptake. Thus, d-amphetamine is equipotent in inhibiting DA uptake and promoting DA release from the synaptic vesicles, whereas in comparison, lobeline more potently (28-fold ) inhibits DA uptake compared with its ability to evoke DA release from synaptic vesicles and consequently redistribute presynaptic DA storage.

d-Amphetamine has been reported to inhibit ($IC_{50}$18 4 $\mu$M [$^3$H]DA uptake into porcine striatal synaptic vesicles (Philippu and Beyer, 1973; Ary and Komiskey, 1980) and to inhibit ($K_i$~2 $\mu$M) monoamine uptake into human VMAT2 expressed in CV-1 cells (Erickson et al., 1996). Also, d-amphetamine has been reported to inhibit [$^3$H]DTBZ binding to rat striatal homogenates ($K_i$>20 $\mu$M) (Rostene et al., 1992) and human VMAT2 expresed in COS cells ($K_i$= 300 $\mu$M) (Gonzalez et al, 1994). The present result that d-amphetamine inhibits ($IC_{50}$=39 $\mu$M) [$^3$H]DTBZ binding to rat striatal synaptic vesicle membranes is consistent with the latter work. The discrepancy between the d-amphetamine concentration that inhibits [$^3$H]DA uptake into synaptic vesicles and that which inhibits [$^3$H]DTBZ binding may be explained by differences in the assay preparations or by species differences. More likely, d-amphetamine inhibits DA uptake into synaptic vesicles via a different mechanism or site, i.e., not through an interaction with the TBZ site or VMAT2. Reserpine binds to VMAT2 via the substrate recognition site, a site that is distinct from the TBZ binding site (Henry and Scherman, 1989; Liu et al., 1996). Methamphetamine, which is a compound structurally similar to d-amphetamine, has been reported to potently inhibit binding ($IC_{50}$=0.40 $\mu$M) to the reserpine site on VMAT2 expressed in CHO cells (Peter et al., 1994). Thus, d-amphetamine may interact with the reserpine site to inhibit vesicular monoamine uptake.

Furthermore, it is well established that VMAT activity in vesicles requires both a proton gradient and a membrane potential for monoamine transport (Johnson and Scarpa, 1976, 1979; Johnson et al., 1979; Kanner et al., 1980; Harnadek et al., 1985; Russel et al., 1985; Brownstein and Hoffman, 1994). d-amphetamine has been reported to disrupt the vesicular proton gradient required for VMAT2 activity, releasing DA from synaptic vesicles of P. corneus giant DA cells, increasing the cytosolic concentration of DA, and promoting its reverse transport (Sulzer and Rayport, 1990; Sulzer et al., 1995). As a result of the acidic environment (pH 5.6) inside the synaptic vesicle (Johnson, 1988), lobeline and d-amphetamine molecules, once inside the vesicle, become protonated with a concomitant generation of hydroxyl ion. The amount of hydroxyl ion generated by these compounds should correlate with their ability to disrupt the vesicle proton gradient and further with their ability to evoke DA release from the vesicles. In comparison with d-amphetamine, which has a $pK_a$ of 9.9 (Sulzer and Rayport, 1990), lobeline is a weaker base with a $pK_a$ of 8.3 (Barlow and Johnson, 1989). When only the $pK_a$ values of lobeline and d-amphetamine and the pH value inside the vesicles are considered, the ratio of the amount of hydroxyl ion generated by an equivalent molar amount of d-amphetamine and lobeline can be calculated using the Henerson-Hasselbach equation (Martin et al., 1993). The calculation reveals that d-amphetamine is 40-fold more potent in generating hydroxyl ion than the same molar amount of lobeline, and thus one would predicte a 40-fold higher potency for d-amphetamine to evoke vesicleuar DA release compared to lobeline. However, results from the present study show that d-amphetamine is only 10-fold more potent than lobeline in releasing DA from the synaptic vesicles. Therefore, the present results are not consistent with the theoretical calculation when only the influence of the drugs on the vesicular proton gradient is taken into consideration, suggesting that other mechanisms may also be involved in lobeline-induced vesicular DA release.

Another difference between lobeline and d-amphetamine is lipophilicity. The 1-octanol/water partition coefficient values (log p) for d-amphetamine and lobeline are 1.76 (experimentally determined; Hansch et al., 1995) and 3.84 (calculated; E. J. Lien, personal communication). Since lobeline has greater lipophilicity than d-amphetamine, lobeline may penetrate cell membranes to a greater extent and reach a higher intracellular concentration than amphetamine. This could explain the discrepancy between the observed molar potencies of lobeline and d-amphetamine to evoke DA release from synaptic vesicles and the calculated relative molar potencies predicted by disruption of the proton gradient.

When striatal slices are superfused with lobeline, vesicular DA uptake is inhibited, and at higher concentrations, vesicular DA release is promoted. The concentrations of lobeline that inhibit [$^3$H]DTBZ binding are congruent with those that inhibit vesicular DA uptake and evoke DOPAC overflow from striatal slices; however, concentrations of lobeline that evoke DA release from synaptic vesicles are 28-fold higher. Therefore, taken together, the results suggest that lobeline primarily inhibits vesicular DA uptake via an interaction with the TBZ site on VMAT2. The interaction with VMAT2 alters presynaptic DA storage and increases cytosolic DA concentrations and its subsequent metabolism, leading to DOPAC overflow from rat striatal slices. In contrast, superfusion of striatal slices with d-amphetamine evokes DA overflow (Parker and Cubeddu, 1986; Dwoskin et al., 1988), resulting from an increase in the cytosolic DA via augmentation of vesicular DA release and inhibition of vesicular DA uptake (possibly via the substrate recognition site on VMAT2). Because d-amphetamine inhibits monoamine oxidase (Mantle et al., 1976; Miller et al., 1980), the increased extravesicular, cytosolic DA is available for release from the terminal by reversal of DAT (Liang and Rutledge, 1982). In contrast to d-amphetamine, lobeline does not inhibit monoamine oxidase, and DOPAC overflow from rat striatal slices is observed. The resulting DOPAC (rather than DA) overflow as a consequence of lobeline's interaction at the dopaminergic presynaptic terminal may be in part responsible for lobeline's apparent lack of addiction liability compared to d-amphetamine.

More recently, studies have suggested that normal or intact synaptic vesicle function may be necessary for amphetamine-conditioned reward, as indicated by diminished amphetamine-induced conditioned place preference in VMAT2 knockout mice compared with wild-type mice (Takahashi et al., 1997). The present results suggest that the mechanism of the effect of amphetamine on synaptic vesicle function is similar to, but clearly different from, that of lobeline. Interestingly, lobeline does not produce conditioned place preference (Fudala and Iwamoto, 1986; Stolerman et al., 1995), supporting its apparent lack of addiction liability. Furthermore, lobeline's effect on synaptic vesicles appears to be mechanistically more similar to that of TBZ because inhibition of DA uptake into the vesicle is its primary action. TBZ has been used therapeutically in Huntington's disease (Standaert and Young, 1996) and apparently lacks addiction liability. Thus, the specific nature of the alteration of synaptic vesicle function may in part determine the neuropharmacological profile of these drugs, particularly with regard to their reinforcing effects.

Thus, lobeline alters presynaptic DA storage, either by inhibiting DA uptake ($IC_{50}$=0.88 $\mu$M) into synaptic vesicles via an interaction with the DTBZ site ($IC_{50}$=0.90 $\mu$M) or by promoting release of DA from the vesicles ($EC_{50}$=25 $\mu$M). Additionally, lobeline binds to the nicotinic receptor with a high affinity ($K_i$ 5–30 nM) (Lippiello and Fernandes, 1986; Broussolle et al., 1989), ~2 orders of magnitude higher than its affinity for the TBZ site. However, lobeline does not act as an agonist at the nicotinic receptor to evoke DA release from presynaptic terminals in striatum. Lobeline may be acting as an antagonist at the nicotinic receptor on the presynaptic dopaminergic nerve terminal. As nicotine is believed to activate dopaminergic systems and evoke DA release, resulting in its reinforcing effect (Fibiger and Phillips, 1987; Corrigall et al., 1992, 1994), the lobeline-induced alteration in dopaminergic function at the level of the synaptic vesicle and/or its potential antagonist action at nicotinic receptors may explain its therapeutic use as a substitution agent for cessation of tobacco smoking.

In summary, lobeline evoked [$^3$H]overflow from rat striatal slices preloaded with [$^3$H]DA, in a concentration-dependent, calcium-independent and mecamylamine-insensitive manner. A lobeline-induced inhibition of synaptic vesicular DA transport and subsequent redistribution of presynaptic DA storage may be the mechanism by which lobeline evokes DA release. Clearly, lobeline evokes DA release by a mechanism different from that of nicotine, which may explain the reported differences in the behavioral effects of these drugs, and the differences in their abilities to upregulate nicotinic receptors following chronic administration.

The present results do not support a nicotinic mechanism of action for lobeline as an agonist but rather suggest that the mechanism of action of lobeline is via an alteration of presynaptic DA storage resulting primarily from inhibition of vesicular DA uptake via the TBZ site on VMAT2. Furthermore, lobeline's mechanism of action at the level of the synaptic terminal is similar to, but subtly different from, that of d-amphetamine.

Although the present invention has been discussed hereinabove by way of examples for the purpose of illustration and clarity of understanding, it should be appreciated that the scope of the invention is instead defined by the appended claims and equivalents thereof.

REFERENCES

The pertinent disclosures of the references listed below and as discussed above are incorporated herein by reference.

AIZENMAN, E., "Effects of nicotinic agonists on the NMDA receptor," *Brain Res.*, 551:355–357 (1991).

ANDERSON, D. J. et al., "Nicotine receptor binding of [$^3$H]cytisine, [$^3$H]nicotine and [$^3$H]methylcarbamylcholine in rat brain," *Eur. J. Pharmacol.*, 253:261–267 (1994).

ARY T. E. et al. "Phencyclidine: effect on theaccumulation of $^3$H-dopamine in synaptic vesicles," *Life Sci.* 26: 575–578 (1980).

BANERJEE, S. et al., "Nicotine antagonists: phosphoinositide turnover and receptor binding to determine muscarinic properties," *Medical Pharmacol.*, 38(17):2933–2935 (1989).

BARLOW, R. B. et al., "Relationship between structure and nicotine-like activity: X-ray crystal structure analysis of (−)cytisine and (−)lobeline hydrochloride and a comparison with (−)nicotine and other nicotine-like compounds," *Br. J. Pharmacol.*, 98:799–808 (1989).

BEERS, M. F. et al., "Evidence for an ascorbate shuttle for the transfer of reducing equivalents across chromaffin granule membranes," *J. Biol. Chem.*, 261:2529–2535 (1986).

BENOWITZ, N. L. et al., "Pharmacokinetics, metabolism, and pharmacodynamics of nicotine," In *Nicotine Psychopharmacology: Molecular, Cellular, and Behavioral Aspects*, ed. by S. Wonnacott, et al., pp.112–157, Oxford University Press, 1990.

BENWELL, M. E. M. et al., "The effects of acute and repeated nicotine treatment on nucleus accumbens dopamine and locomotor activity," *Br. J. Pharmacol.*, 105:849–856 (1992).

BENWELL, M. E. M. et al., "Evidence that tobacco smoking increases the density of (−)-[$^3$H]nicotine binding sites in human brain," *J. Neurochem.* 50 (4):1243–1247 (1988).

BHAT, R. V. et al., "Regulation of brain nicotinic receptors by chronic agonist infusion," *J. Neurochem.*, 56(6):1932–1939 (1991).

BHAT, R. V. et al., "Effects of chronic nicotine infusion on kinetics of high-affinity nicotine binding," *J. Neurochem.*, 62:574–581 (1994).

BRAZELL, M. P. et al., "Acute administration of nicotine increases the in vivo extracellular levels of dopamine, 3,4-dihydroxyphenylacetic acid and ascorbic acid preferentially in the nucleus accumbens of the rat: comparison with the caudateputamen," *Neuropharmacol.*, 29:1177–1185 (1990).

BRIONI, J. D. et al., "Nicotinic receptor agonists exhibit anxiolytic-like effects on the elevated plus-maze test," *Eur. J. Pharmacol.*, 238:1–8 (1993).

BROWNSTEIN, M. J. et al., "Neurotransmitter transporters," *Rec. Prog. Hormone Res.*, 49:27–42 (1994).

BROUSSOLLE, E. P. et al., "In vivo binding of $^3$H-nicotine in the mouse brain," *Life Sci.*, 44:1123–1132 (1989).

CHESSELET, M. F., "Presynaptic regulation of neurotransmitter release in the brain: Facts and hypotheses," *Neurosci.*, 12:347–375 (1984).

CLARKE, P. B. S., "Dopaminergic mechanisms in the locomotor stimulant effects of nicotine," *Biochem. Pharmacol.* 40:1427–1432 (1990).

CLARKE, P. B. S. et al., "The effect of nicotine on locomotor activity in non-tolerant and tolerant rats," *Br. J. Pharmacol.*, 78:329–337 (1983a).

CLARKE, P. B. S. et al., "Characterization of the locomotor stimulant action of nicotine in tolerant rats," *Br. J. Pharmacol.*, 80:587–594 (1983b).

CLARKE, P. B. S. et al., "Apparent absence of nicotine-induced conditioned place preference in rats," *Psychopharmacol.*, 92:84–88 (1987).

CLARKE, P. S. et al., "Autoradiographic evidence for nicotine receptors on nigrostriatal and mesolimbic dopaminergic neurons," *Brain Res.*, 348:355–358 (1985).

COLLINS, A. C. et al., "Dissociation of the apparent relationship between nicotine tolerance and up-regulation of nicotinic receptors," *Brain Res. Bull.*, 25:373–379 (1990).

CORRIGAL, W. A. et al., "The mesolimbic dopaminergic system is implicated in the reinforcing effects of nicotine," *Psychopharmacol.*, 107:285–289 (1992).

CORRIGAL, W. A. et al., "Self-administered nicotine activates the mesolimbic dopamine system through the ventral tegmental area," *Brain Res.*, 653:278–284 (1994).

COURT, J. A. et al., "Nicotine reduces the binding of [$^3$H]MK-801 to brain membranes, but not via the stimulation of high-affinity nicotinic receptors." *Brain Res.*, 524:319–321 (1990).

CUBEDDU, L. X. et al., "Metabolism and efflux of [$^3$H]dopamine in rat neostriatum: Presynaptic origin of 3,4-[$^3$H]dihydroxyphenylacetic acid," *J. Pharmacol. ExP. Ther.*, 209:165–175 (1979).

DAMSMA, G. et al., "Lack of tolerance to nicotine-induced dopamine release in the nucleus accumbens," *Eur. J. Pharmacol.*, 168:363–368 (1989).

DEBLER, E. A. et al., "Ascorbic acid and striatal transport of [$^3$H]1-methyl-4-phenylpyridine (MPP$^+$) and [$^3$H] dopamine," *Life Sci.*, 42:2553–2559 (1988).

DECKER, M. W. et al., "Diversity of neuronal nicotinic acetylcholine receptors: lessons from behavior and implications for CNS therapeutics," *Life Sci.*, 56:545–570 (1995).

DECKER, M. W. et al., "Effects of lobeline, a nicotinic receptor agonist, on learning and memory," *Pharmacol. Biochem. Behav.*, 45:571–576 (1993).

DONNY, E. C. et al.: "Nicotine self-administration in rats," *Psychopharmacol.* (in press).

DORSEY, J. L., "Control of the tobacco habit," *Ann Int. Med.*, 10:628–631 (1936).

DUBOCOVICH, M. L. et al., "Binding characteristics of the dopamine uptake inhibitor [$^3$H]nomifensine to striatal membranes," *Biochem. Pharmacol.*, 34 (8):1137–1144 (1985).

DWOSKIN, L. P. et al., "Robust modulation of [$^3$H] dopamine release from rat striatal slices by D-2 dopamine receptors," *J. Pharmacol. Exp. Ther.*, 239:442–453 (1986).

DWOSKIN L. P., et al., "Uptake and release of dopamine from rat striatal slices: comparison of PCP, amphetamine and nomifensine," in *Pharmacology and Functional Regulation of Dopamine Neurons* (Beart P. M., Woodruff G. N. , and Jackson D. M., eds), pp. 248–250. Macmillan Press, Basingstoke (1988).

ERICKSON, J. D. et al., "Chloride ion increases [$^3$H] dopamine accumulation by synaptic vesicles purified from rat striatum: inhibition by thiocyanate ion," *Brain Res.*, 516:155–160 (1990).

ERICKSON, J. D., et al. "Distinct pharmacological properties and distribution in neurons and endocrine cells of two isoforms of the human vesicular monoamine transporter," *Proc. Natl. Acad. Sci. USA*, 93, 5166–5171 (1996).

FIBIGER, H. C. et al. "Role of catecholamine transmitters in brain reward systems: implications for the neurobiology of affect," in *Brain Reward Systems and Abuse* (Engle J. and Oreland L., eds), pp. 61–74. Raven Press, New York (1987).

FISCHER, J. F. et al., "Chemical release of dopamine from striatal homogenates: evidence for an exchange diffusion model," *J.Pharmacol.Exp.Ther.*, 208 (2):203–209, (1979).

FLOOR E., et al. "Dynamic storage of dopamine in rat brain synaptic vesicles in vitro," *J. Neurochem.* 64, 689–699 (1995).

FUDALA, P. J. et al., "Further studies on nicotine-induced conditioned place preference in the rat," *Pharmacol. Biochem. Behav.*, 25:1041–1049 (1986).

FUDALA, P. J., et al., "Pharmacologic characterization of nicotine-induced conditioned place preference," *Pharmacol. Biochem. Behav.*, 22:237–241 (1985).

FUNG, Y. K. et al., "Receptor mechanisms of nicotine-induced locomotor hyperactivity in chronic nicotine treated rats," *Eur. J. Pharmacol.*, 152:263–271 (1988).

GELLER, I. et al., "Effects of nicotine monomethiodide, lobeline, chlordiazepoxide, meprobamate and caffeine on a discrimination task in laboratory rats," *Psychopharmacol. (Berl.)*, 20:355–365 (1971).

GIORGUIEFF-CHESSELET, M. F. et al., "Regulation of dopamine release by presynaptic nicotinic receptors in rat striatal slices: effect of nicotine in a low concentration," *Life Sci.*, 25:1257–1262 (1979).

GONZALEZ, A. M. et al., "Synaptic vesicular monoamine transporter expression: distribution and pharmacologic-profile," *Mol. Brain Res.*, 22:219–226 (1994).

GRADY, S. et al., "Characterization of nicotine receptor-mediated $^3$H-dopamine release from synaptosomes prepared from mouse striatum," *J. Neurochem.*, 59:848–856 (1992).

GRADY, S. R., et al., "Desensitization of nicotine-stimulated [$^3$H]dopamine release from mouse striatal synaptosomes," *J. Neurochem.*, 62:1390–1398 (1994).

GRAHAM, D. G., et al., "Autoxidation versus covalent binding of quinones as the mechanism of toxicity of dopamine, 6-hydroxydopamine, and related compounds towards C1300 neuroblastoma cells in vitro," *Mol. Pharmacol.*, 14:644–653 (1978).

HAMANN, S. R. et al., "Hyperalgesic and analgesic actions of morphine, U50-488, naltrexone, and (–)lobeline in the rat brainstem," *Pharmacol. Biochem. Behav.*, 47:197–201 (1994).

HANSCH C., et al. "Exploring QSAR hydrophobic, electronic and steric constants," in *American Chemical Society Professional Reference Book*. American Chemical Society, Washington, D.C. (1995).

HARNADEK G. J., et al. "An electron Transfer dependent membrane potential in chromaffin vesicle ghosts," *Biochemistry* 24, 384–389 (1985).

HARSING, L. G. et al., "Dopamine efflux from striatum after chronic nicotine: evidence for autoreceptor desensitization," *J. Neurochem.*, 59:48–54 (1992).

HART, C. et al., "Nicotine effects on dopamine clearance in rat nucleus accumbens," *J. Neurochem.*, 66 (1):216–221, (1996).

HENRY J. P. et al. "Radioligands of the vesicular monoamine transporter and their use as markers of monoamine storage vesicles," *Biochem. Pharmacol.* 38, 2395–2404 (1989).

HURD, Y. L. et al., "Ca$^{2+}$ dependence of the amphetamine, nomifensine, and Lu 19-005 effect on in vivo dopamine transmission," *Eur. J. Pharmacol.*, 166:261–269 (1989).

IMPERATO, A. et al., "Nicotine preferentially stimulates dopamine release in the limbic system of freely moving rats," *Eur. J. Pharm.*, 132:337–338 (1986).

IZENWASSER, S. et al., "Nicotine indirectly inhibits [$^3$H]dopamine uptake at concentrations that do not directly promote [$^3$H]dopamine release in rat striatum," *J. Neurochem.*, 56 (2):603–610 (1991).

JOHNSON R. G. et al. "Internal pH of isolated chromaffin vesicles," *J. Biol. Chem.* 251, 2189–2191 (1976).

JOHNSON R. G. et al. "Protonmotive force and catecholamine transport in isolated chromaffin granules," *J. Biol. Chem.* 254, 3750–3760 (1979).

JOHNSON R. G. et al. "Biological amine transport in chromafifin ghosts," *J. Biol. Chem.* 254, 10963–10972 (1979).

JOHNSON, R. G., "Accumulation of biological amines into chromaffin granules: a model for hormone and neurotransmitter transport," *Physiol. Rev.*, 68:232–307 (1988).

JOHNSON, K. M. et al., "Pharmacological evidence for N-methyl-D-aspartate receptors on nigrostriatal dopaminergic nerve terminals," *Can. J. Physiol. Pharmacol.*, 69:1416–1421 (1991).

KALYUZHNYY, V. V., "The treatment of nicotinism with the aid of lobeline and its influence on vegetative and vascular reactions," *J. Neural. Psychiat.*, 68:1864–1870 (1968).

KANNER B. I., et al. "Electrogenic transport of biogenic amines in chromaffin granule membrane vesicles," *FEBS Lett.* 111, 83–86 (1980).

KILBOURN M., et al. "Binding of α-dihydrotetrabenazine to the vesicular monamine transporter is stereoselective," *Eur. J. Pharmacol.* 278, 249–252 (1985).

KNEPPER, S. M. et al., "Inhibition of norepinephrine transport into synaptic vesicles by amphetamine analogs," *J. Pharmaco. Exp. Ther.*, 247(2):487–494 (1988).

KRAMER, H. K. et al., "The effect of nicotine on catecholaminergic storage vesicles," *Brain Res.*, 503:296–298 (1989).

LEVI, G. et al., "Carrier-mediated release of neurotransmitters," *TINS.*, 16(10):415–419 (1993).

LIANG, N. Y. et al.: "Comparison of the release of [$^3$H]dopamine from isolated corpus striatum by amphetamine, fenfluramine and unlabelled dopamine," *Biochem. Physiol.*, 31:983–992 (1982).

LIPPIELLO, P. M. et al., "The binding of L-[$^3$H]nicotine to a single class of high affinity sites in rat brain membrane," *Mol. Pharmacol.*, 29:448–454 (1986).

LIU Y., et al. "A molecular analysis of vesicular amine transporter," *Behav. Brain Res.* 73, 51–58 (1996).

LOIACONO, R. et al., "Multiple binding sites for nicotine receptor antagonists in inhibiting [$^3$H] (–)-nicotine binding in rat cortex," *Neuropharmacol.*, 32:847–853 (1993).

MANTLE T. J., et al. "Inhibition of monoamine oxidase by amphetamine and related compounds," *Biochem. Pharmacol.* 25, 2073–2077 (1976).

MARTIN A., et al. "Buffer and isotonic solution," in *Physical Pharmacy* (Martin A., Bustamante P., and Chun A. H. C., eds), pp. 169–189. Lea & Fibiger, Philadelphia (1993).

MARKS, M. J. et al., "Nicotine binding and nicotinic receptor subunit RNA after chronic nicotine treatment," *J. Neurosci.*, 12(7):2765–2784 (1992).

MASSERANO, J. M. et al., "Effects of chronic cocaine administration on [$^3$H]dopamine uptake in the nucleus accumbens, striatum and frontal cortex of rats," *J. Pharmacol. Exp. Ther.*, 270(1):133–141 (1994).

MILLER H. J., et al. "In vivo monoamine oxidase inhibition by d-amphetamine," *Biochem. Pharmacol.* 29, 1347–1354 (1980).

NUNN-THOMPSON et al., "Pharmacotherapy for smoking cessation," *Clin. Pharmacy.*, 8:710–720 (1989).

OLIN, B. R. et al., "Smoking Deterrents," In *Drug Facts and Comparisons*. 1995 edition, ed. by B. R. Olin et al., pp. 3087–3095, St. Louis, Mo.: J. B. Lippincott Co., 1995.

PARKER, E. M. et al., "Effects of d-amphetamine and dopamine synthesis inhibitors on dopamine and acetylcholine neurotransmission in the striatum. I. Release in the absence of vesicular transmitter stores," *J. Pharmacol. Exp. Ther.*, 237(1):179–192 (1986).

PENG, O. et al., "Nicotine-induced increase in the neuronal nicotinic receptors results from a decrease in the rate of receptor turnover," *Mol. Pharmacol.*, 46:523–530 (1994).

PETER D., et al. "The chromaffin granule and synaptic vesicle amine transporters differ in substrate recognition and sensitivity to inhibitors," *J. Biol. Chem.* 269, 7231–7237 (1994).

PHILIPPU A. et al. "Dopamine and noradrenaline transport into subcellular vesicles of the striatum," *Naunyn Schmiedebergs Arch. Pharmacol.* 278, 387–402 (1973).

PLETSCHER A., et al. "Benzoquinolizine derivatives: a new class of monoamine decreasing drugs with psychotropic action," *Int. Rev. Neurobiol.* 4, 275–306 (1962).

PRIGNOT, J., "Pharmacological approach to smoking cessation," *Eur. Respir. J.*, 2:550–560 (1989).

RAPIER, C. et al., "Stereoselective nicotine-induced release of dopamine from striatal synaptosomes: concentration dependent and repetitive stimulation," *J. Neurochem.*, 50(4):1123–1130 (1988)

RAPIER, C. et al., "Nicotine modulation of [$^3$H] dopamine release from striatal synaptosomes: pharmacological characterization," *J. Neurochem.*, 50:1123–1130 (1990).

REAVILL, C. et al.: "High affinity binding of [$^3$H](–)-nicotine to rat brain membranes and its inhibition by analogues of nicotine," *Neuropharmacol.*, 27(3):235–241 (1988).

REAVILL, C. et al., "Behavioral and pharmacokinetics studies on nicotine, cytosine and lobeline," *Neuropharmacol.*, 29(7):619–624 (1990).

REYNOLDS, I. J. et al., "[$^3$H]MK801 binding to the N-methyl-D-aspartate receptor reveals drug interactions with zinc and magnesium binding sites," *J. Pharmacol. Exp. Ther.*, 247(3):1025–1031 (1988).

ROMANO, C. et al., "Sterespecific nicotine receptors on rat brain membranes," *Science*, 210:647–650 (1980).

ROMM, E. et al., "Purification of L-[$^3$H]nicotine eliminates low affinity binding," *Life Sci.*, 46:935–946 (1990).

ROSS, B. et al., "Uptake of some tritiated sympathomimetic amines by mouse brain cortex slices in vitro," *Acta Pharmacologica*, 24:297–309 (1966).

ROSTENE W., et al. "Dopamine transporter: pharmacological distinction between the synaptic membrane and the vesicular transporter in rat striatum," *Eur. J. Pharmacol.* 218, 175–177 (1992).

ROWELL, P. P.: "Nanomolar concentrations of nicotine increase the release of [$^3$H]dopamine from rat striatal synaptosomes," *Neurosci. Lett.*, 189:171–175 (1995).

ROWELL, P. P. et al., "Apparent inability of nicotine to inhibit dopamine uptake into rat striatal tissue in vitro," *The Pharmacologist.*, 35:134 (1993).

ROWELL, P. P. et al., "Desensitization of nicotine-stimulated dopamine release from rat striatal synaptosomes," *The Pharmacologist*, 34:154 (1992).

ROWELL, P. P. et al., "Characterization of nicotine-induced desensitization of evoked dopamine release from rat striatal synaptosomes," *J. Neurochem.*, 63:561–569 (1994).

ROWELL, P. P. et al., "Stimulation of [$^3$H]dopamine release by nicotine in rat nucleus accumbens," *J. Neurochem.*, 49:1149–1154 (1987).

RUSSELL J. T., et al. "Electron transfer across posterior pituitary neurosecretory vesicle membranes," *J. Biochem.* 260, 226–231 (1985).

SAKURAI, Y. et al., "Enhancement of [$^3$H]dopamine release and its [$^3$H]metabolites in rat striatum by nicotinic drugs," *Brain Res.*, 242:99–106 (1982).

SANDERSON, E. M. et al., "Upregulation of nicotinic receptors following continuous infusion of nicotine is brain-region-specific," *Brain Res.*, 617:349–352 (1993).

SACAAN, A. I. et al., "Pharmacological characterization of neuronal acetylcholine gated ion channel receptor-mediated hippocampal norepinephrine and striatal dopamine release from rat brain slices," *J. Pharmacol. Exp. Ther.*, 274(1):224–230 (1995).

SCHECHTER, M. D. et al., "Nicotine as a discriminative cue in rats: inability of related drugs to produce a nicotine-like cuing effect," *Psychopharmacol. (Berl.)*, 27:379–387 (1972).

SCHERMAN D. "Dihydrotetrabenazine binding and monoamine uptake in mouse brain regions," *J. Neurochem.* 47, 331–339 (1986).

SCHERMAN D., et al. "The regionalization of [$^3$H] dihydrotetrabenazine binding sites in the mouse brain and its relationship to the distribution of monoamines and their metabolites," *Brain Res.* 370, 176–181 (1986).

SCHERMAN D., et al. "[$^3$H]Dihydrotetrabenazine, a new in vitro monoaminergic probe for human brain," *J. Neurochem.* 50, 1131–1136 (1988).

SCHULDINER, S. et al., "Amphetamine derivatives interact with both plasma membrane and secretory vesicle biogenic amine transporter," *Mol. Pharmacol.*, 44:1227–1231 (1993).

SHOAIB, M. et al., "Nicotine-induced place preferences following prior nicotine exposure in rat," *Psychopharmacol.*, 113:445–452 (1984).

SLIVKA, A. et al., "Hydroxyl radical attack on dopamine," *J. Biol. Chem.*, 260:15446–15472 (1985).

SLOAN, J. W. et al., "The competitive binding characteristics of nicotinic ligands and their pharmacology," *Pharmacol. Biochem. Behav.*, 30:255–267 (1988).

SONSALLA, P. K., "The role of N-methyl-D-aspartate receptors in dopaminergic neuropathology produced by the amphetamines," *Drug Alcohol Depend.*, 37:101–105 (1995).

STANDAERT D. G. et al. "Treatment of central nervous system degenerative disorders," in *The Pharmacological Basis of Therapeutics*, 9th ed. (Hardman J. G., Limberd L. E., Molinoff P. B., Ruddon R. W., and Gilman A. G., eds), pp. 503–519, McGraw-Hill, New York (1996).

STOLERMAN, I. P. et al., "Dissociation between the locomotor stimulant and depressant effects of nicotinic agonists in rats," *Psychopharmacol.*, 117:430–437 (1995).

SULZER, D. et al., "Amphetamine and other psychostimulants reduce pH gradient in midbrain dopaminergic neurons and chromaffin granules: A mechanism of action," *Neurons*, 5:797–808 (1990).

SULZER, D. et al., "Amphetamine redistributes dopamine from synaptic vesicles to the cytosol and promotes reverse transport," *J. Neurosci.*, 15(5):4102–4108 (1995).

TAKAHASHI, N. et al. "VMAT2 knockout mice: heterozygotes display reduced amphetamine-conditioned reward, enhanced amphetamine locomotion, and enhanced MPTP toxicity," *Proc. Natl. Acad. Sci. USA*, 94(18): 9938–9943 (1997).

TAKANO, Y. et al., "Presynaptic modulation of the release of dopamine from striatal synaptosomes: difference in the effects of high K$^+$ stimulation, methamphetamine and nicotinic drugs," *Brain Res.*, 279:330–334 (1983).

TOTH, E. et al., "Effect of nicotine on extracellular levels of neurotransmitters assessed by microdialysis in various brain regions: Role of glutamic acid," *Neurochem. Res.*, 17:265–271 (1992).

VARANDA, W. A. et al., "The acetylcholine receptor of the neuromuscular junction recognizes mecamylamine as a noncompetitive antagonist," *Mol. Pharmacol.*, 28:128–137 (1985).

VINCENT M. S. et al. "Purification of [$^3$H] dihydrotetrabenazine-binding protein from bovine adrenal medulla," *J. Pharmacol. Exp. Ther.* 40, 889–894 (1991).

WESTFALL, T. C. et al., "Effect of nicotine and other drugs on the release of [$^3$H]norepinephrine and [$^{14}$C] dopamine in rat brain striatum and hypothalamus slices," *Neuropharmacol.*, 13:1025–1032 (1974).

WESTFALL, T. C. et al., "Effect of nicotine and related substances upon amine levels in the brain," *Ann. N.Y. Acad. Sci.*, 142:83–100 (1967).

WESTFALL, T. C. et al., "Mechanisms of nicotine regulation of dopamine release in neostriatum," In *Tobacco Smoking and Nicotine*, ed. by W. R. Martin et al., pp. 209–223 Plenum, New York, 1987.

WRIGHT, I. S. et al., "Lobeline sulfate: Its pharmacology and use in the treatment of the tobacco habit," *JAMA*, 109:649–654 (1937).

YAMADA, S. et al., "Brain nicotinic acetylcholine receptors biochemical characterization by neosurugatoxin," *Mol. Pharmacol.*, 28:120–127 (1985).

YAMASHITA, H. et al., "Effect of nicotine on dopamine uptake in COS cells possessing the rat dopamine transporter and in PC12 cell," *Biochem. Pharmacol.*, 49(5):742–745 (1995).

ZACZEK, R. et al., "Interactions of [$^3$H]amphetamine with rat brain synaptosomes. II. Active transport," *J. Pharmacol. Exp. Ther.*, 257:830–835 (1991).

ZUMSTEIN, A. K. et al.: "Pathways of dopamine metabolism in rabbit caudate nucleus in vitro," *Naunyn-Schmiedeberg's Arch. Pharmacol.*, 316:205–217 (1981).

What is claimed is:

1. A method of blocking dopamine uptake into a presynaptic terminal or vesicle comprising administering to an individual an effective amount of a compound having the formula

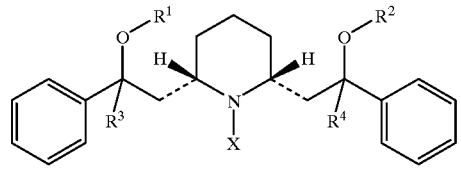

wherein R$^1$ and R$^2$ are independently H, lower alkyl, lower alkenyl, lower alkylcarbonyl, phenylcarbonyl, alkylphenylcarbonyl, lower alkoxycarbonyl, lower alkylaminocarbonyl, higher alkylcarbonyl, and poly (alkyleneoxide) carbonyl; R$^3$ is H or combines with R$^1$ to form a double bond; R$^4$ is H or combines with R$^2$ to form a double bond; and X is H or lower alkyl, or pharmaceutically acceptable salt thereof.

2. The method of claim 1, wherein the compound is selected from the group consisting of lobeline, lobelanidine, lobelanine, and pharmaceutically acceptable salts thereof.

3. The method of claim 1, wherein the compound is lobeline, and pharmaceutically acceptable salts thereof.

4. The method of claim 1, wherein said administering is performed subcutaneously, intramuscularly, intravenously, transdermally, orally, intranasally, or rectally.

5. The method of claim 1, wherein the blockage of dopamine uptake occurs at a presynaptic dopamine transporter.

6. The method of claim 1, wherein the blockage of dopamine uptake occurs at a vesicular monoamine transporter.

7. The method according to claim 6, wherein said vesicular monoamine transporter is VMAT2.

8. The method of claim 1, wherein the blockage of dopamine uptake occurs at the presynaptic dopamine transporter and vesicular monoamine transporter.

9. The method according to claim 8, wherein said vesicular monoamine transporter is VMAT2.

10. A method of treating an individual having a central nervous system disease or pathology comprising administering to the individual an effective amount of a compound having the formula

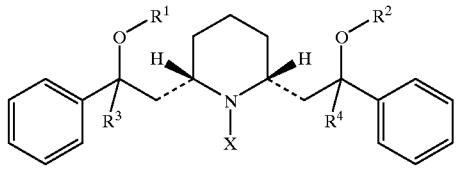

wherein $R^1$ and $R^2$ are independently H, lower alkyl, lower alkenyl, lower alkylcarbonyl, phenylcarbonyl, alkylphenylcarbonyl, lower alkoxycarbonyl, lower alkylaminocarbonyl, higher alkylcarbonyl, and poly(alkyleneoxide) carbonyl; $R^3$ is H or combines with $R^1$ to form a double bond; $R^4$ is H or combines with $R^2$ to form a double bond; and X is H or lower alkyl, or pharmaceutically acceptable salt thereof, wherein the central nervous system disease or pathology is selected from the group consisting of head or brain trauma, psychosis, sleep disorders, obsessive-compulsive disorders, panic disorders, myasthenia gravis, Parkinson's disease, schizophrenia, Tourette's syndrome, Huntington's disease, and attention deficit disorder.

11. The method of claim 10, wherein the compound is selected from the group consisting of lobeline, lobelanidine, lobelanine, and pharmaceutically acceptable salts thereof.

12. The method of claim 10, wherein the compound is lobeline, and pharmaceutically acceptable salts thereof.

13. The method of claim 10, wherein said administering is performed subcutaneously, intramuscularly, intravenously, transdermally, orally, intranasally, or rectally.

* * * * *